US012718440B2

(12) United States Patent
Kobayashi et al.

(10) Patent No.: US 12,718,440 B2
(45) Date of Patent: Aug. 25, 2026

(54) ATTENUATION COEFFICIENT IMAGE GENERATION METHOD, NUCLEAR MEDICINE DIAGNOSTIC APPARATUS, AND TRAINED MODEL GENERATION METHOD

(71) Applicant: Shimadzu Corporation, Kyoto (JP)

(72) Inventors: Tetsuya Kobayashi, Kyoto (JP); Yui Shigeki, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 655 days.

(21) Appl. No.: 18/012,846

(22) PCT Filed: Jun. 26, 2020

(86) PCT No.: PCT/JP2020/025275
§ 371 (c)(1),
(2) Date: Dec. 23, 2022

(87) PCT Pub. No.: WO2021/260928
PCT Pub. Date: Dec. 30, 2021

(65) Prior Publication Data

US 2023/0281889 A1 Sep. 7, 2023

(51) Int. Cl.
*G06T 12/10* (2026.01)
*A61B 6/00* (2024.01)
(Continued)

(52) U.S. Cl.
CPC .............. *G06T 12/10* (2026.01); *A61B 6/037* (2013.01); *A61B 6/4057* (2013.01); *A61B 6/501* (2013.01);
(Continued)

(58) Field of Classification Search
CPC . G06T 11/005; G06T 11/006; G06T 2210/41; G06T 11/008; A61B 6/037;
(Continued)

(56) References Cited

U.S. PATENT DOCUMENTS

| | | | | |
|---|---|---|---|---|
| 11,234,666 | B2 * | 2/2022 | Chan | A61B 6/5258 |
| 2010/0204563 | A1 | 8/2010 | Stodilka et al. | |

(Continued)

FOREIGN PATENT DOCUMENTS

| | | | |
|---|---|---|---|
| CN | 104220898 | A | 12/2014 |
| JP | 2010-008164 | A | 1/2010 |

(Continued)

OTHER PUBLICATIONS

Tonghe Wang et al Mar. 2020, Physics of Medical Imaging (Year: 2020).*

(Continued)

*Primary Examiner* — Gregory A Morse
*Assistant Examiner* — Ty Mitchell Beatty
(74) *Attorney, Agent, or Firm* — Muir Patent Law, PLLC

(57) ABSTRACT

This attenuation coefficient image generation method includes a step of generating an input image (6), a step of generating an intermediate image (7) including an image relating to tissue areas based on the input image (6), and a step of generating an attenuation coefficient image (9) based the intermediate image (7) and known attenuation coefficients of tissue areas.

23 Claims, 17 Drawing Sheets

(51) Int. Cl.

| | |
|---|---|
| ***A61B 6/03*** | (2006.01) |
| ***A61B 6/40*** | (2024.01) |
| ***A61B 6/50*** | (2024.01) |
| ***G06T 12/20*** | (2026.01) |

(52) U.S. Cl.
CPC ............ *A61B 6/502* (2013.01); *A61B 6/5205* (2013.01); *A61B 6/5217* (2013.01); *A61B 6/5282* (2013.01); *G06T 12/20* (2026.01); *G06T 2210/41* (2013.01)

(58) Field of Classification Search
CPC ....... A61B 6/4057; A61B 6/501; A61B 6/502; A61B 6/5205; A61B 6/5217; A61B 6/5282; A61B 6/5235; A61B 6/5294; G01T 1/161
See application file for complete search history.

(56) References Cited

U.S. PATENT DOCUMENTS

| | | | |
|---|---|---|---|
| 2013/0077844 | A1 | 3/2013 | Vija et al. |
| 2015/0117736 | A1 | 4/2015 | Yamaya et al. |
| 2016/0026900 | A1 | 1/2016 | Ando |
| 2018/0061059 | A1* | 3/2018 | Xu .......................... G06T 7/174 |
| 2018/0197317 | A1* | 7/2018 | Cheng ................... G06T 11/006 |
| 2019/0130569 | A1 | 5/2019 | Liu et al. |
| 2019/0266728 | A1* | 8/2019 | Lee ........................ A61B 6/037 |
| 2019/0336095 | A1 | 11/2019 | Ritter et al. |
| 2020/0085397 | A1 | 3/2020 | Kobayashi |
| 2021/0104313 | A1 | 4/2021 | Mizobe et al. |

FOREIGN PATENT DOCUMENTS

| | | | |
|---|---|---|---|
| JP | 2013-185855 | A | 9/2013 |
| JP | 2019-531783 | A | 11/2019 |
| WO | 2018-220686 | A1 | 12/2018 |
| WO | 2019-172181 | A1 | 9/2019 |
| WO | 2019-240257 | A1 | 12/2019 |

OTHER PUBLICATIONS

Xue Dong et al 2019 Phys. Med. Biol. 64 215016 (Year: 2019).*
Yang J et al Epub Feb. 23, 2017. PMID: 28234560. (Year: 2017).*
Habib Zaidi et al 1999 Division of Nuclear Medicine, Geneva University Hospital (Year: 1999).*
Notice of Reasons for Refusal dated Dec. 19, 2023 for corresponding Japanese Patent Application No. 2022-532213.
Liu et al. "Deep learning MR imaging-based attenuation correction for PET/MR imaging." Radiology 286.2 (2018): 676-684.
Written Opinion by the International Searching Authority for PCT application PCT/JP2020/025275, dated Aug. 25, 2020.
First Office Action dated Apr. 2, 2025 for corresponding Chinese Patent Application No. 202080102355.5.
Jaewon Yang et al., "Quantitative Evaluation of Atlas-based Attenuation Correction for Brain PET in an Integrated Time-of Flight PET/MR Imaging System", Journal of Nuclear Medicine. vol. 284, First period, pp. 169-179, Feb. 23, 2017.
Second Office Action dated Nov. 28, 2025, for corresponding Chinese Patent Application No. 202080102355.5.

* cited by examiner

FIG. 9

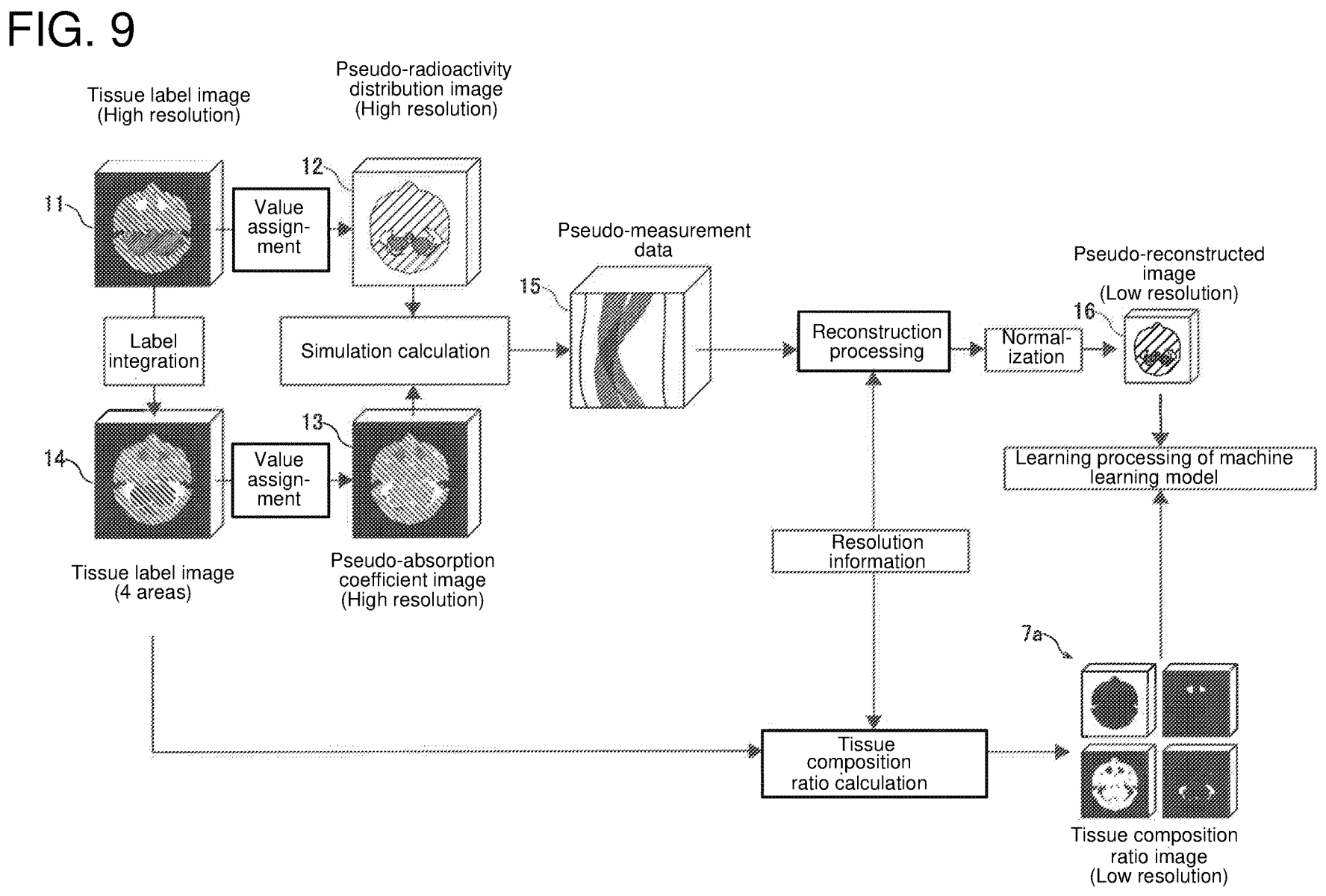

Tissue label image (High resolution)
11
Value assign-ment
12
Pseudo-radioactivity distribution image (High resolution)
Label integration
Simulation calculation
14
Tissue label image (4 areas)
Value assign-ment
13
Pseudo-absorption coefficient image (High resolution)
15
Pseudo-measurement data
Reconstruction processing
Resolution information
Tissue composition ratio calculation
Normal-ization
16
Pseudo-reconstructed image (Low resolution)
Learning processing of machine learning model
7a
Tissue composition ratio image (Low resolution)

Second modification

FIG. 12

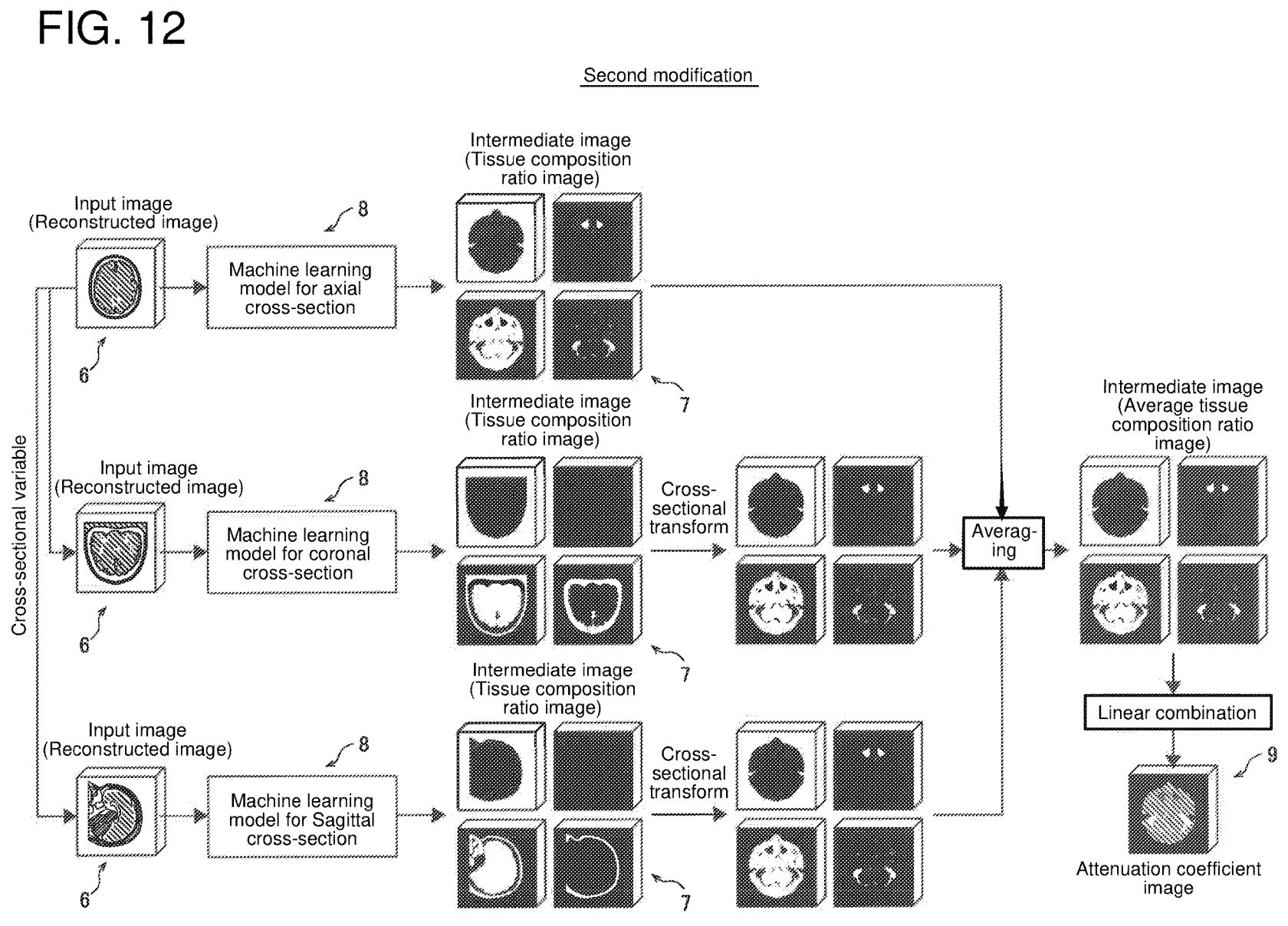

Second modification

Cross-sectional variable

Input image (Reconstructed image) 6

Machine learning model for axial cross-section 8

Intermediate image (Tissue composition ratio image) 7

Input image (Reconstructed image) 6

Machine learning model for coronal cross-section 8

Intermediate image (Tissue composition ratio image) 7

Cross-sectional transform

Input image (Reconstructed image) 6

Machine learning model for Sagittal cross-section 8

Intermediate image (Tissue composition ratio image) 7

Cross-sectional transform

Averaging

Intermediate image (Average tissue composition ratio image)

Linear combination

9

Attenuation coefficient image

Fourth modification

Fifth modification

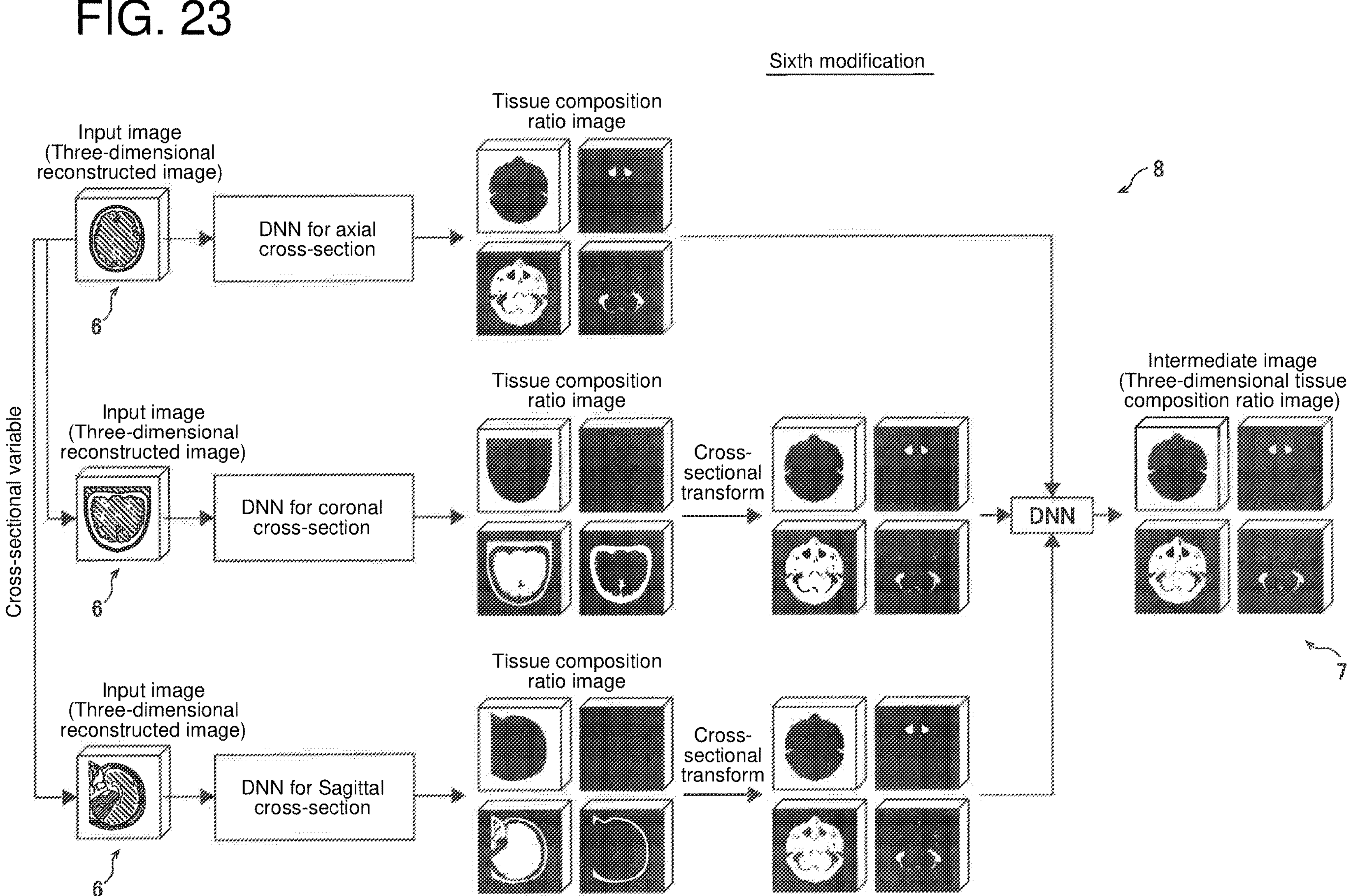
FIG. 23
Sixth modification
Input image (Three-dimensional reconstructed image)
6
DNN for axial cross-section
Tissue composition ratio image
Input image (Three-dimensional reconstructed image)
6
DNN for coronal cross-section
Tissue composition ratio image
Cross-sectional transform
Input image (Three-dimensional reconstructed image)
6
DNN for Sagittal cross-section
Tissue composition ratio image
Cross-sectional transform
Cross-sectional variable
8
DNN
Intermediate image (Three-dimensional tissue composition ratio image)
7

ATTENUATION COEFFICIENT IMAGE GENERATION METHOD, NUCLEAR MEDICINE DIAGNOSTIC APPARATUS, AND TRAINED MODEL GENERATION METHOD

TECHNICAL FIELD

The present invention relates to an attenuation coefficient image generation method, a nuclear medicine diagnostic apparatus, and a trained model generation method.

BACKGROUND ART

Conventionally, a method for generating an attenuation coefficient image for a nuclear medicine diagnostic apparatus is known. Such a method is disclosed, for example, in U.S. Patent Application Publication No. 2019/0130569 (hereinafter simply referred to as "Patent Document 1").

The above-described Patent Document 1 discloses a method for generating an attenuation coefficient image for a positron emission tomography imager (nuclear medicine diagnostic apparatus). In this method, a machine learning model trained in advance is used to generate an attenuation coefficient image. Specifically, a PET image generated from PET (Positron Emission Tomography) data is input to a machine learning model. Then, an attenuation coefficient image is output from the machine learning model. With this, the attenuation coefficient image is generated from the PET data (measurement data) by the machine learning model without performing CT (Computed Tomography) imaging, MR (Magnetic Resonance) imaging or the like on a subject.

PRIOR ART DOCUMENT

Patent Document

Patent Document 1: U.S. Patent Application Publication No. 2019/0130569

SUMMARY OF THE INVENTION

Problems to be Solved by the Invention

In the method described in the above-described Patent Document 1, an attenuation coefficient image can be generated from PET data (measurement data) by a machine learning model without performing CT imaging and MR imaging or the like on a subject. However, in a case where a machine learning model outputs an attenuation coefficient image, it is not considered whether the attenuation coefficient of the attenuation coefficient image is a value (usual value) within an appropriate range. Therefore, there is a possibility that the attenuation coefficient of the attenuation coefficient image takes a value (unusual value) outside an appropriate range. For this reason, it is difficult to eliminate the possibility that the attenuation coefficient of the attenuation image takes a value outside an appropriate range while generating an attenuation coefficient image from PET data (measurement data) by a machine learning model, without performing CT imaging or MR imaging on a subject.

The present invention has been made to solve the above-described problems. It is an object of the present invention to provide an attenuation coefficient image generation method and a nuclear medicine diagnostic apparatus capable of ensuring that an attenuation coefficient of an attenuation coefficient image takes a value (usual value) within an appropriate range even in a case where an attenuation coefficient image is generated from measurement data without performing CT imaging, MR imaging, or the like, on a subject.

Means for Solving the Problems

In order to attain the above-described object, an attenuation coefficient image generation method according to a first aspect of the present invention is an attenuation coefficient image generation method for a nuclear medicine diagnostic apparatus, the method being configured to generate an attenuation coefficient image of a subject. The method includes the steps of:

generating an input image by performing imaging processing on measurement data acquired based on detection of radiation emitted from the subject;

generating an intermediate image including an image relating to tissue areas based on the input image; and generating an attenuation coefficient image based on the intermediate image and known attenuation coefficients of the tissue areas.

Here, the term 'tissue' refers to, for example, a brain, a bone, a skin, a muscle, an internal organ, and an internal cavity.

A nuclear medicine diagnostic apparatus according to a second aspect of the present invention includes:

a detector configured to detect radiation generated from a radiopharmaceutical agent in a subject; and a processor configured to generate a radioactivity distribution image of the subject based on detection of the radiation by the detector, wherein the processor is configured to generate an input image by performing imaging processing on measurement data acquired based on detection of the radiation emitted from the subject, generate an intermediate image including an image relating to tissue areas based on the input image, and generate an attenuation coefficient image for generating the radioactivity distribution image, based on the intermediate image and known attenuation coefficients of the tissue areas.

Further, a trained model generation method according to a third aspect of the present invention is a trained model generation method for a nuclear medicine diagnostic apparatus. The method includes the steps of:

preparing tissue label images indicating a tissue to which each pixel belongs;

generating pseudo-radioactivity distribution images and pseudo-attenuation coefficient images, based on the tissue label images;

generating pseudo-measurement data by performing simulation calculations, based on the pseudo-radioactivity distribution images and the pseudo-attenuation coefficient images;

generating pseudo images by performing imaging processing on the pseudo-measurement data; and generating a trained model using the pseudo images as training data.

Effects of the Invention

In the attenuation coefficient image generation method according to the first aspect of the present invention and the nuclear medicine diagnostic apparatus according to the second aspect of the present invention, as described above, an input image is generated by performing imaging processing on measurement data acquired based on detection of radiation emitted from the subject, an intermediate image including an image relating to tissue areas is generated based on the input image, and an attenuation coefficient image is generated based on the intermediate image and known attenuation coefficients of the tissue areas. With this configuration, an attenuation coefficient image can be generated based on the intermediate image including the image relating to the tissue area. Consequently, even in a case where an attenuation coefficient image is generated from measurement data without performing CT imaging, MR imaging, or the like, on a subject, it is possible to ensure that the attenuation coefficient of the attenuation coefficient image takes a value (usual value) within an appropriate range.

Further, in the trained model generation method according to the third aspect of the present invention, as described above, the method includes the steps of: preparing tissue label images indicating a tissue to which each pixel belongs; generating pseudo-radioactivity distribution images and pseudo-attenuation coefficient images, based on the tissue label images; generating pseudo-measurement data by performing simulation calculations, based on the pseudo-radioactivity distribution images and the pseudo-attenuation coefficient images; generating pseudo-image by performing imaging processing on the pseudo measurement data; and generating a trained model using the pseudo images as training data. This makes it possible to generate a trained model using pseudo images acquired by simulation calculations as training data. Consequently, unlike the case where a trained model is generated using actual images (clinical images) as training data, there is no need to collect a large number of clinical images. As a result, it is possible to generate a trained model without collecting a large number of clinical images that is not easy from the viewpoint of protecting personal information.

BRIEF DESCRIPTION OF THE DRAWINGS

FIG. 9 is a diagram for explaining details of training a machine learning model according to one embodiment.

FIG. 12 is a diagram for explaining generation of an attenuation coefficient image from an intermediate image according to a second modification of one embodiment.

FIG. 23 is a diagram for explaining a machine learning model according to a sixth modification of one embodiment.

EMBODIMENTS FOR CARRYING OUT THE INVENTION

Hereinafter, some embodiments in which the present invention is embodied will be described with reference to the attached drawings.

(Configuration of PET Device)

Figure 1:
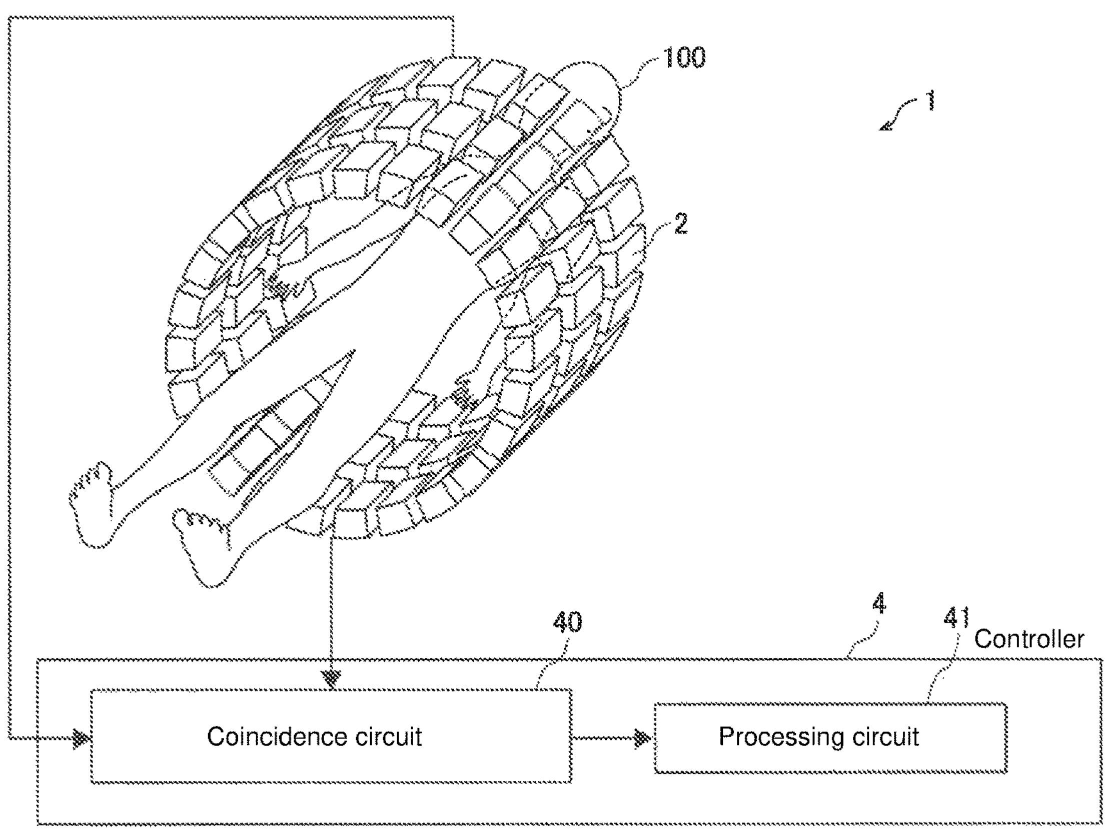
FIG. 1 is a schematic diagram showing a configuration of a PET device according to one embodiment.
Figure 2:
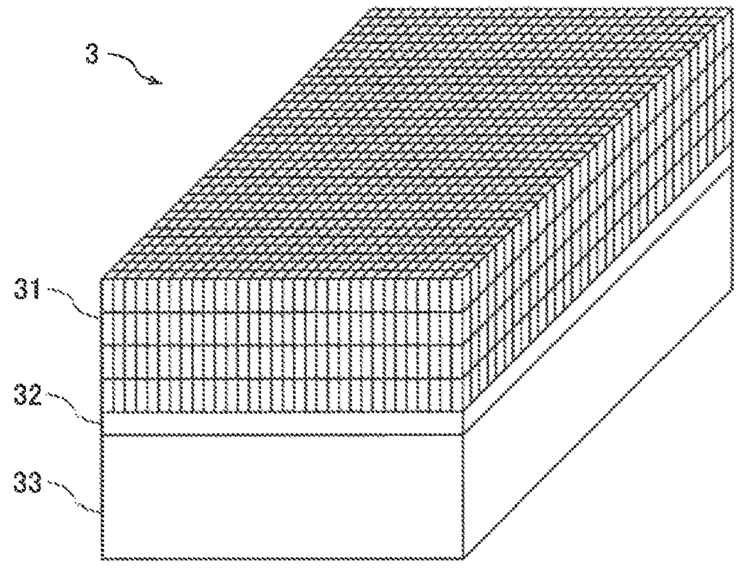
FIG. 2 is a schematic perspective view showing a configuration of a radiation (γ-rays) detector according to one embodiment.

With reference to FIG. 1 and FIG. 2, a configuration of a PET (Positron Emission Tomography) device 1 according to one embodiment will be described.

As shown in FIG. 1, the PET device 1 is a device for imaging a subject 100 by detecting radiation (γ-rays) generated from an inside of the subject 100 due to a radiopharmaceutical agent that has been administered to the subject 100 in advance. The subject 100 is a human. The γ-rays are annihilation radiation generated in the subject 100 due to pair annihilation between a positron generated from the radiopharmaceutical agent and an electron of the atom in the vicinity of the positron. The PET device 1 is configured to generate a radioactivity distribution image 10 (see FIG. 3) of the subject 100 based on the imaging result of the subject 100. Note that the PET device 1 may be configured to capture an image of the entire body of the subject 100, or may be configured to capture a part (e.g., a breast, a head) of the subject 100. The PET device 1 is one example of the "nuclear medicine diagnostic apparatus" recited in claims.

The PET device 1 is provided with a detector ring 2 surrounding the subject 100. The detector ring 2 is provided in such a manner that a plurality of layers is laminated in the body axis direction of the subject 100. Inside the detector ring 2, a plurality of radiation (γ-rays) detectors 3 (see FIG. 2) is provided. With this configuration, the detector ring 2 is configured to detect radiation (γ-rays) generated from a radiopharmaceutical agent in the subject 100. Note that the detector ring 2 is one example of the "detector" recited in claims.

Further, the PET device 1 is provided with a controller 4. The controller 4 includes a coincidence circuit 40 and a processing circuit 41. Note that in FIG. 1, only two wiring from the radiation detector 3 (see FIG. 2) to the controller 4 (coincidence circuit 40) is shown. However, the wiring is connected to the controller 4 (coincidence circuit 40) by the total number of channels of photomultiplier tubes (PMT: Photo Multiplier Tube) 33 (see FIG. 2) (described later) of the radiation detector 3. Note that the processing circuit 41 is one example of the "processor" as recited in claims. In some cases, a sensor, such as, e.g., a SiPM (Silicon Photomultiplier), other than a PMT, may be used.

As shown in FIG. 2, the radiation detector 3 includes a scintillator block 31, a light guide 32, and a photomultiplier tube 33. Note that in some cases, the light guide 32 is not used.

The scintillator block 31 converts the radiation (γ-rays) generated from the subject 100 (see FIG. 1) to which a radiopharmaceutical agent has been administered into light. When a radiopharmaceutical agent is administered to the subject 100, two radiation (γ-rays) are generated due to the disappearance of the positron of a positron release type RI (Radio Isotope). Each scintillator element constituting the scintillator block 31 emits light in accordance with the incidence of radiation (γ-rays) to convert the radiation (γ-rays) into the light.

The light guide 32 is optically coupled to each of the scintillator block 31 and the photomultiplier tube 33. The light emitted at the scintillator element of the scintillator block 31 is diffused in the scintillator block 31 and is input to the photomultiplier tube 33 via the light guide 32.

The photomultiplier tube 33 multiplies the light input through the light guide 32 and converts it into an electric signal. This electric signal is transmitted to the coincidence circuit 40 (see FIG. 1).

The coincidence circuit 40 (see FIG. 1) generates detection signal data (count value) based on the electric signal transmitted from the photomultiplier tube 33.

Specifically, the coincidence circuit 40 (see FIG. 1) checks the position of the scintillator block 31 and the incidence timing of the radiation (γ-rays). Only when radiation (γ-rays) is simultaneously incident on two scintillator blocks 31 positioned on both sides (on the diagonal centered on the subject 100) of the subject 100, the coincidence circuit 40 determines that the transmitted electric signal is proper data. That is, the coincidence circuit 40 detects that radiation (γ-rays) is simultaneously observed (i.e., coincidence) in two radiation detectors 3 on both sides (diagonal centered on the subject 100) of the subject 100 based on the electric signal described above.

The detection signal data (count value) configured by the proper data determined to be coincidence by the coincidence circuit 40 is transmitted to the processing circuit 41 (see FIG. 1). The processing circuit 41 generates a radioactivity distribution image 10 (see FIG. 3) of the subject 100 based on the detection of the radiation (γ-rays) by the detector ring 2.

(Generation of Radioactivity Distribution Image)

Next, the radioactivity distribution image generation processing by the PET device 1 according to one embodiment will be described with reference to the flowchart shown in FIG. 3 and diagrams shown in FIG. 4 to FIG. 6. Note that the radioactivity distribution image generation processing is performed by the processing circuit 41 of the controller 4.

Figure 3:
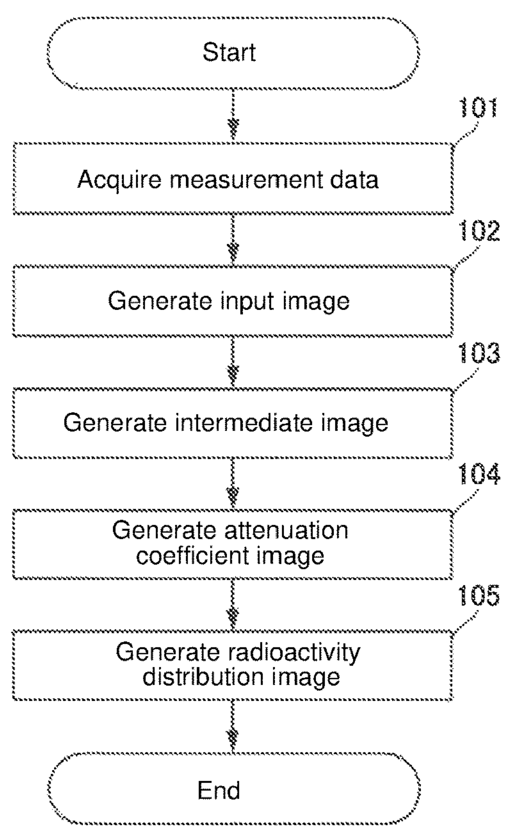
FIG. 3 is a flowchart for explaining radioactivity distribution image generation processing according to one embodiment.
Figure 4:
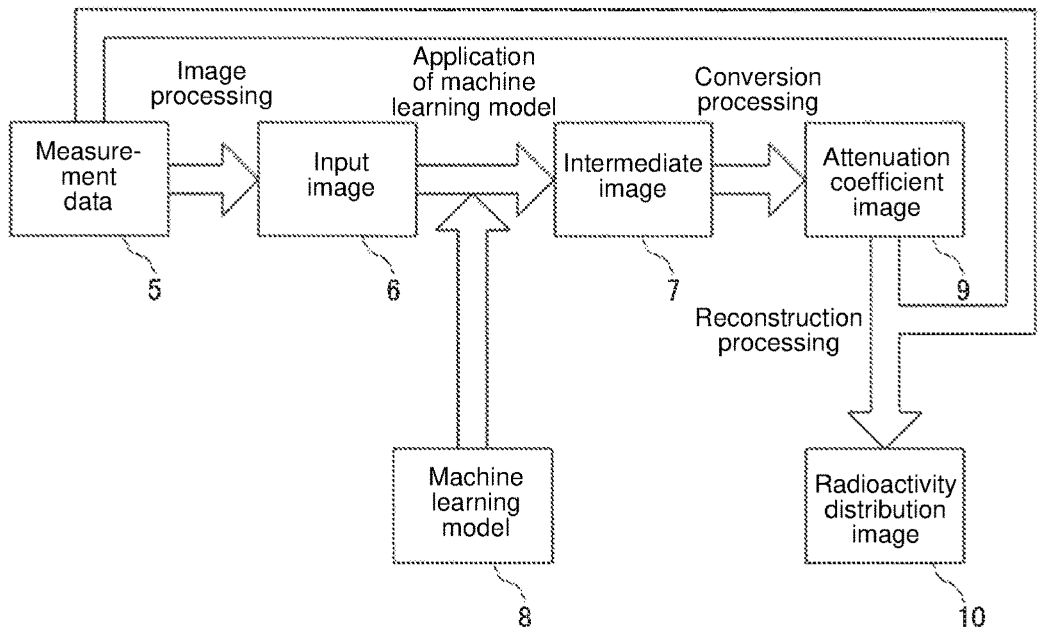
FIG. 4 is a diagram for explaining generation of a radioactivity distribution image according to one embodiment.

As shown in FIG. 3 and FIG. 4, in Step 101, first, measurement data 5 is acquired based on the detection of the radiation emitted from the subject 100.

Then, in Step 102, an input image 6 is generated by performing imaging processing on the measurement data 5. Specifically, in Step 102, an input image 6 is generated by performing processing including imaging processing by histogram, imaging processing by machine learning, or back projection processing. As the imaging processing based on histogram, it is possible to adopt an imaging method in which an event is added to the most probable position, based on TOF (Time Of Flight) information included in the measurement data 5. Further, as the imaging processing by machine learning, a method can be adopted in which imaging is performed using a machine learning model that converts measurement data 5 into an input image 6. Further, as the processing including back projection processing, for example, simple back projection processing, reconstruction processing, or the like can be adopted. Further, as the reconstruction processing, for example, analytical reconstruction processing, iterative reconstruction processing, or the like can be adopted. Further, as the analytical reconstruction processing, for example, an FBP (Filtered Back Projection) method or the like can be adopted. As the iterative reconstruction processing, for example, an OSEM (Ordered Subsets Expectation Maximization) method or the like can be adopted. In Step 102, for example, reconstruction processing is performed. In this case, the input image 6 is a reconstructed image.

The input image 6 is an image showing the inside of the subject 100. The input image 6 includes at least one of a three-dimensional image, an axial cross-sectional image, a coronal cross-sectional image, a sagittal cross-sectional image, a patch image extracting a partial area from a three-dimensional image, a patch image extracting a partial area from an axial cross-sectional image, and a patch image extracting a partial area from a sagittal cross-sectional image. Here, the term "cross-sectional image" refers to a one-slice of a two-dimensional image. The axial cross-sectional image refers to an image of a cross-section perpendicular to the body axis. Further, the coronal cross-sectional image refers to an image of a cross-section parallel to the body axis. The sagittal cross-sectional image refers to an image of a longitudinal cross-section parallel to the body axis. The input image 6 may be only one slice or several consecutive slices of cross-sectional images.

Further, in Step 102, an input image 6 is generated without performing at least one of attenuation correction processing and scatter correction processing. The attenuation correction processing denotes processing for correcting the attenuation of the radiation in the subject 100. The scatter correction processing denotes processing for correcting the scatter of radiation in the subject 100. In Step 102, an input image 6 with no correction in which at least one of attenuation correction processing and scatter correction processing is not performed is generated from the measurement data 5.

Further, in Step 102, image quality conversion processing may not be performed, image quality conversion processing may be performed, or area identification processing may be performed. In this embodiment, the input image 6 may include at least one of an image to which quality conversion processing has not been applied, an image to which quality conversion processing has been applied, and an image to which area identification processing has been applied. As the image quality conversion processing, for example, γ correction processing, histogram equalization processing, smoothing processing, edge detection processing, and the like can be adopted. Further, for example, as the image quality conversion processing, processing of adding random noise of distribution, such as, e.g., uniform distribution, normal distribution, Poisson distribution, and Laplace distribution, can be adopted. Further, for example, as the image quality conversion processing, processing of multiplying the entire image or a particular area of an image by a constant may be employed. Further, for example, as the area identification processing, processing of identifying the contour of the subject 100 in the image can be adopted.

Then, in Step 103, an intermediate image 7 including images relating to tissue areas is generated based on the input image 6. Specifically, in Step 103, the intermediate image 7 is generated by applying the machine learning model 8 trained in advance to the input image 6. The machine learning model 8 is a machine learning model in which the input image 6 is input and the intermediate image 7 is output. The machine learning model 8 includes at least one of a machine learning model in which a three-dimensional image is input, a machine learning model in which an axial cross-sectional image is input, a machine learning model in which a coronal cross-sectional image is input, a machine learning model in which a sagittal cross-sectional image is input, a machine learning model in which a patch image extracted from a three-dimensional image is input, a machine model in which a patch image extracted from an axial cross-sectional image is input, a machine model in which a patch image extracted from a coronal cross-sectional image is input, and a machine learning model in which a patch image extracted from a sagittal cross-sectional image is input.

Note that in figures (FIG. 5, FIG. 6, and FIG. 8) of this embodiment, for convenience of explanation, an example of a machine learning model 8 is shown in which an input image 6, which is an axial cross-sectional image, is input, and an intermediate image 7 corresponding to the axial cross-sectional image is output.

The intermediate image 7 is composed of a combination of N pieces (finite number) of tissues with known attenuation coefficients, such as, e.g., a brain, a bone, a skin, a muscle, and an internal organ. For example, in a case where the measurement data 5 is measurement data of a human head, elements (tissues) constituting an image relating to tissue areas of the intermediate image 7 include at least one of a background (outside of a subject), a cavity (e.g., a nasal and an oral cavity), a soft tissue (e.g., a brain and a skin), and a bone (skull). Further, for example, in a case where the measurement data 5 is measurement data of a human breast, the elements (tissues) constituting an image relating to the tissue area of the intermediate image 7 include at least one of a background (outside of a subject) and a soft tissue.

Figure 5:
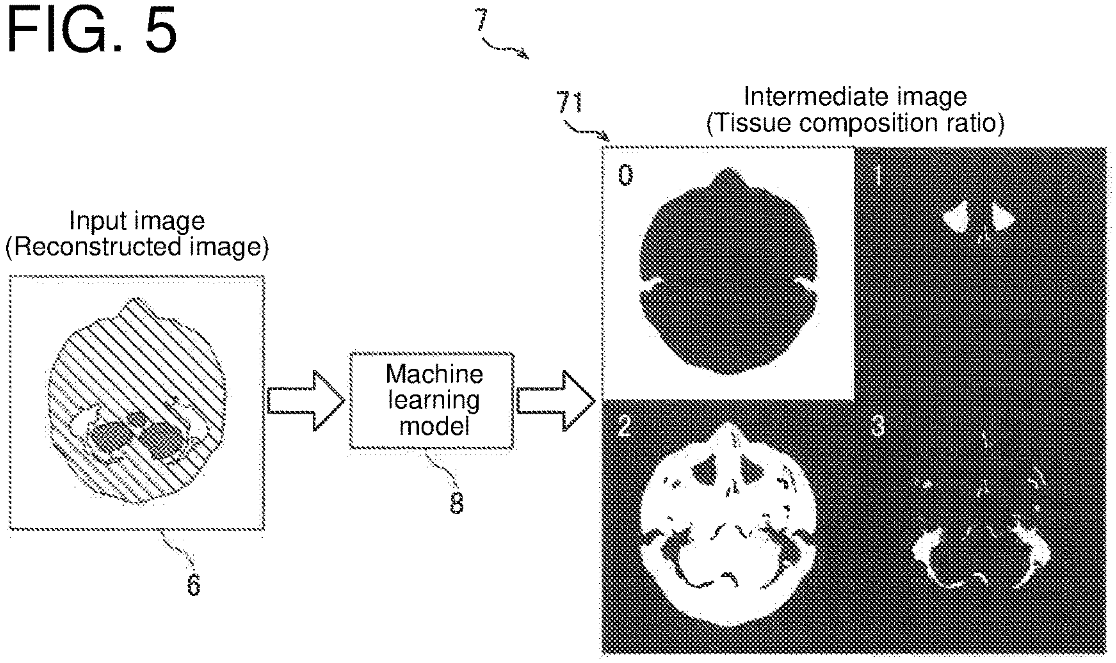
FIG. 5 is a diagram for explaining generation of an intermediate image from an input image according to one embodiment.
Figure 6:
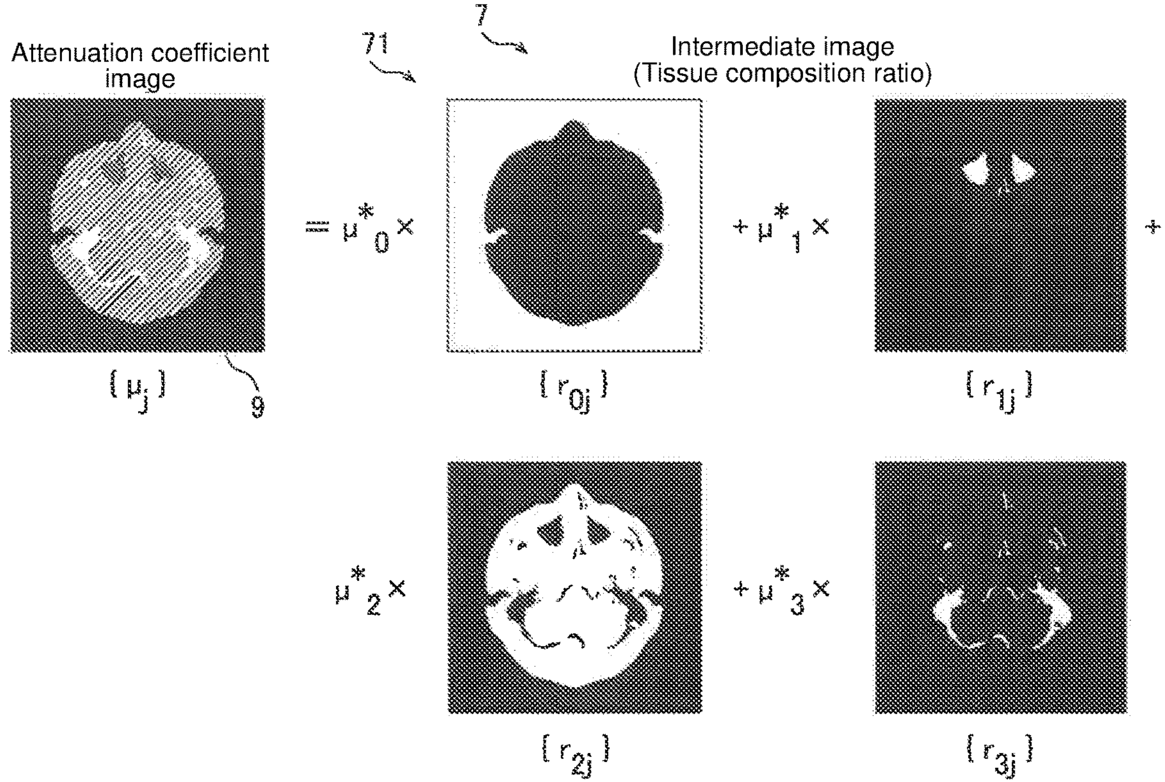
FIG. 6 is a diagram for explaining generation of an attenuation coefficient image from an intermediate image according to one embodiment.

In this embodiment, as shown in FIG. 5, the intermediate image 7 includes a tissue composition ratio image 71 indicating the ratio of tissues included in each pixel as an image relating to tissue areas. The tissue composition ratio image 71 is a multi-channel image in which a ratio of a plurality of tissues included in each pixel is shown as a pixel value. In the example shown in FIG. 5, the tissue composition ratio image 71 is an image of a human head and includes four channels of images, i.e., a background image channel, a cavity image channel, a soft tissue image channel, and a bone image channel. The image of a background channel is configured such that the ratio of the background included in each pixel is shown as a pixel value. Further, the image of a cavity channel is configured such that the ratio of the cavity included in the pixel is shown as a pixel value. Further, the image of a soft tissue channel is configured such that the ratio of the soft tissue included in each pixel is shown as a pixel value. Further, an image of the bone channel is configured such that the ratio of the bone included in each pixel is shown as a pixel value. Note that, since the pixel value of each image of the four channels indicates the ratio, the sum of pixel values of four channel images for a certain pixel is 1.

Then, as shown in FIG. 3 and FIG. 4, in Step 104, an attenuation coefficient image 9 is generated based on the intermediate image 7 and known attenuation coefficients of tissue areas. In this embodiment, as shown in FIG. 6, in Step 104, an attenuation coefficient is assigned to a tissue in the tissue composition ratio image 71 based on known attenuation coefficients to generate an attenuation coefficient image 9. Specifically, in Step 104, the attenuation coefficient image 9 is generated by performing linear combination processing of tissue composition ratio images 71 of tissues using known attenuation coefficients as weight coefficients. More specifically, linear combination processing of the tissue composition ratio images 71 of tissues using known attenuation coefficients as weight coefficients is performed according to the following Formula (1).

$$\mu_j = \sum_{n=1}^{N} \mu_n^* r_{nj} \tag{1}$$

where, n: Tissue label (tissue number)

j: Pixel number $\mu_j$: Attenuation coefficient of pixel j $\mu^*_n$: Attenuation coefficient (known attenuation coefficient) of tissue n $r_{nj}$: composition ratio of tissue n of pixel j Note that $r_{nj}$ satisfies the following Expression (2).

$$0 \le r_{nj} \le 1, \sum_{n=1}^{N} r_{nj} = 1 \tag{2}$$

For example, in a case where the tissue composition ratio image 71 is an image of a human head and includes images of four channels of a background, a cavity, a soft tissue, and a bone, linear combination processing of the tissue composition ratio images 71 of tissues is performed using known attenuation coefficients as weight coefficients according to Formula (1) described above, using an attenuation coefficient $\mu^*_0$ of a background, an attenuation coefficient of a cavity $\mu^*_1$, an attenuation coefficient $\mu^*_2$ of a soft tissue, an attenuation coefficient $\mu^*_3$ of a bone, which are generally known.

Then, as shown in FIG. 3 and FIG. 4, in Step 105, a radioactivity distribution image 10 is generated by performing reconstruction processing based on the attenuation coefficient image 9 and the measurement data 5. At this time, at least one of attenuation correction processing and scatter correction processing is performed based on the attenuation coefficient image 9. For example, in Step 105, attenuation correction processing is performed based on the attenuation coefficient image 9, and scatter correction processing is performed based on the scatter distribution data acquired based on the attenuation coefficient image 9 and the measurement data 5. In Step 105, a quantitative radioactivity distribution image 10 to which attenuation correction processing and scatter correction processing have been performed is generated.

(Machine Learning Model)

Next, with reference to FIG. 7 to FIG. 9, the machine learning model 8 included in the PET device 1 according to one embodiment will be described. In the following description, the input image 6 and the intermediate image 7 as training data are referred to an input image 6*a* and an intermediate image 7*a*, respectively, for ease of understanding.

Figure 7:
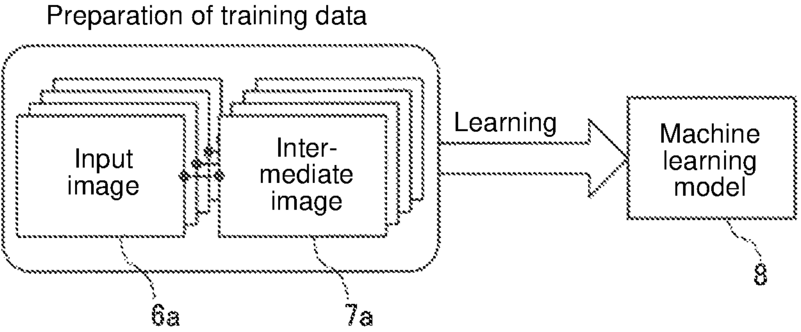
FIG. 7 is a diagram for explaining training of a machine learning model according to one embodiment.

As shown in FIG. 7, the machine learning model 8 is trained by supervised learning using a plurality of pairs of an input image 6*a* and an intermediate image 7*a* as training data. Specifically, the machine learning model 8 is trained such that an input image 6*a* prepared in advance is input and an intermediate image 7*a* prepared in advance is used as a training image (ground truth image). Note that the details of training the machine learning model 8 will be described later.

The machine learning model 8 includes a deep neural network. The deep neural network of the machine learning model 8 includes convolution processing. That is, the machine learning model 8 includes a deep convolutional neural network. As the deep convolutional neural network of the machine learning model 8, for example, a U-shaped network (U-Net) having a skip combination may be adopted. As the activation function of the deep convolutional neural network of the machine learning model 8, a Softmax function may be adopted.

With reference to a flowchart of FIG. 8 and a diagram of FIG. 9, the generation method of the machine learning model 8 (the trained model generation method) included in the PET device 1 according to one embodiment will be described.

Figure 8:
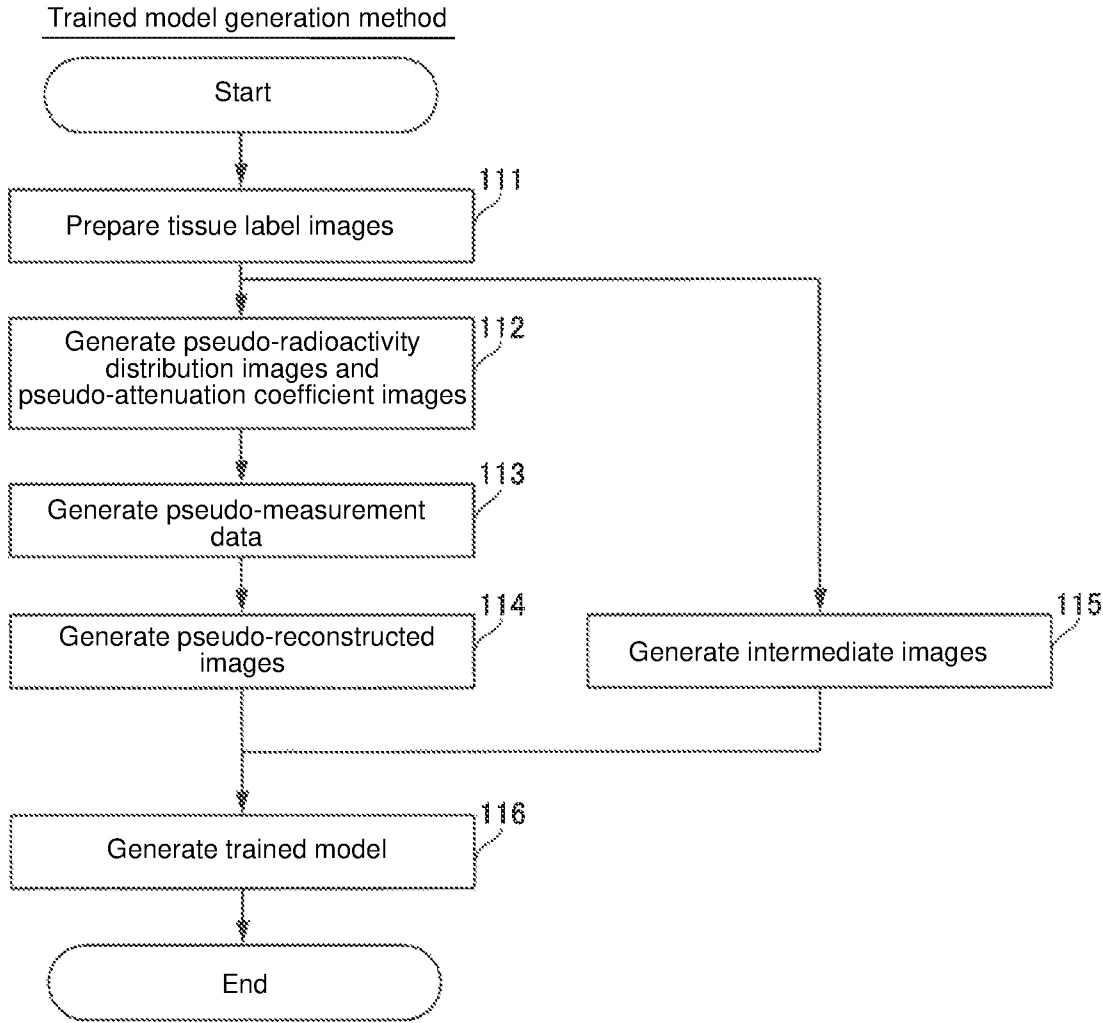
FIG. 8 is a flowchart for explaining a trained model generation method according to one embodiment.

As shown in FIG. 8 and FIG. 9, first, in Step 111, a tissue label image 11 indicating a tissue to which each pixel belongs by a label is prepared. The tissue label image 11 can be prepared by performing area division processing on a medical image, such as, e.g., an MR image and a CT image. The tissue label image 11 can be prepared by acquiring a tissue label image (e.g., BrainWeb) publicly available on the Internet.

Then, in Step 112, a pseudo-radioactivity distribution image 12 and a pseudo-attenuation coefficient image 13 are generated based on a tissue label image 11. Specifically, a pseudo-radioactivity distribution image 12 is generated by assigning radioactive concentration to each tissue of the tissue label image 11. Further, the pseudo-attenuation coefficient image 13 is generated by assigning an attenuation coefficient to each tissue of the tissue label image 14 generated by integrating the label of each tissue of the tissue label image 11. The tissue label image 14 is an image in which the number of labels is reduced for the tissue label image 11 by integrating labels.

Then, in Step 113, the pseudo-measurement data 15 is generated by performing a simulation calculation based on the pseudo-radioactivity distribution image 12 and the pseudo-attenuation coefficient image 13. Specifically, in Step 113, the pseudo-measurement data 15 is generated by inputting the pseudo-radioactivity distribution image 12, the pseudo-attenuation coefficient image 13, and various simulation conditions and performing a simulation calculation. As the simulation calculation, for example, a Monte Carlo simulation calculation, an analytical simulation calculation, or the like can be adopted. In this embodiment, the machine learning model 8 is trained using the pseudo-measurement data 15 generated based on at least one of a Monte Carlo simulation calculation and an analytical simulation calculation. For example, the machine learning model 8 is trained using the pseudo-measurement data 15 generated based on an analytical simulation calculation out of a Monte Carlo simulation calculation and an analytical simulation calculation.

Then, in Step 114, a pseudo-reconstructed image 16 is generated by performing processing (imaging processing) including back projection processing on the pseudo-measurement data 15. Specifically, in Step 114, the pseudo-reconstructed image 16 is generated by performing reconstruction processing by inputting various reconstruction conditions including the pseudo-measurement data 15 and pixel sizes. In the reconstruction processing, resolution information (pixel size information) is input as a parameter. Note that the pseudo-reconstructed image 16 is one example of the "pseudo image" recited in claims.

Further, in Step 114, a normalized pseudo-reconstructed image 16 is generated by performing normalization processing for normalizing the pixel value range to [0, 1] on the pseudo-reconstructed image 16. In Step 114, the normalized pseudo-reconstructed image 16 may be multiplied by a coefficient greater than 0 and smaller than 1. Alternatively, a specific area of the normalized pseudo-reconstructed image 16 or the pseudo-reconstructed image 16 prior to normalization may be multiplied by a positive coefficient. With this, it is possible to train the learning model 8 by the pseudo-reconstructed image 16 with various pixel values. In this embodiment, the input image 6*a* (pseudo-reconstructed image 16) as the training data of the machine learning model 8 includes at least one of a normalized image in which the pixel value range is normalized, an image in which a normalized image is multiplied by a coefficient greater than 0 and smaller than 1, and an image in which a specific area of a normalized image or an image prior to normalization is multiplied by a positive coefficient.

In a case where a normalized image is multiplied by a coefficient greater than 0 and smaller than 1, for example, 1/n (n is a positive integer) is multiplied as a weight coefficient. In this case, a large number of input images 6*a* different in the pixel value magnitude (image brightness) can be generated by setting, e.g., n=2 to 10 (by 1 increment), n=20 to 100 (by 10 increments), and n=200 to 1,000 (by 100 increments).

Further, in a case where a specific area of a normalized image or an image prior to normalization is multiplied by a positive coefficient, an area of a tissue unit can be adopted as the specific area. For example, in a case where a normalized image is an image of a human head, as the specific area, it is possible to adopt a gray matter of a brain, a white matter, a cerebellum, a skin of a head, a muscle of a head, or the like. In this way, it is possible to train the machine learning model 8, considering the diversity of the radioactivity distribution caused by an individual difference and a difference of a radiopharmaceutical agent.

Further, in Step 114, it may be configured such that image quality conversion processing is not performed, image quality conversion processing is performed, or area identification processing is performed. In this embodiment, the input image 6*a* includes at least one of an image to which image quality conversion processing is not applied, an image to which quality conversion processing is applied, and an image to which area identification processing is applied. As the image quality conversion processing, for example, γ correction processing, histogram equalization processing, smoothing processing, edge detection processing, and the like can be adopted. Further, for example, as the image quality conversion processing, processing of adding random noise of a distribution, such as, e.g., a uniform distribution, a normal distribution, a Poisson distribution, and a Laplace distribution, can be adopted. Further, for example, as the image quality conversion processing, processing of multiplying the entire image or a particular area of an image by a constant may be adopted. With this, it is possible to train the machine learning model 8 by input images 6*a* with various pixel values. Further, for example, as the area identification processing, processing of identifying the contour of the subject 100 in the image can be adopted.

Further, in Step 115, an intermediate image 7*a* as training data is generated based on the tissue label image 11. Specifically, in Step 115, based on the tissue label image 14 generated by integrating the tissue labels of the tissue label image 11, an intermediate image 7*a* is generated. More specifically, by assuming the pixel size of the same low resolution as the pseudo-reconstructed image 16 and calculating the ratio (composition ratio) of each tissue included in one pixel with respect to a tissue label image 14 of a high resolution, an intermediate image 7*a* as a tissue composition ratio image is generated.

Then, in Step 116, a machine learning model 8 as a trained model is generated using a large number of pseudo-reconstructed images 16 and intermediate images 7*a* as training data. In this embodiment, the machine learning model 8 is trained using the pseudo-reconstructed image 16 generated based on at least one of a Monte Carlo simulation calculation and an analytical simulation calculation.

Effects of this Embodiment

In this embodiment, the following effects can be obtained.

In this embodiment, as described above, an input image 6 is generated by performing imaging processing on the measurement data 5 acquired based on the detection of the radiation emitted from the subject 100, an intermediate image 7 including an image relating to tissue areas is generated based on the input image 6, and an attenuation coefficient image 9 is generated based on the intermediate image 7 and known attenuation coefficients of the tissue areas. With this, the attenuation coefficient image 9 can be generated based on the intermediate image 7 including images relating to tissue areas. Consequently, even in the case of generating the attenuation coefficient image 9 from the measurement data 5 without performing CT imaging and MR imaging or the like on the subject 100, it is possible to ensure that the attenuation coefficient of the attenuation coefficient image 9 takes a value (usual value) within an appropriate range.

Further, in this embodiment, as described above, the intermediate image 7 includes the tissue composition ratio image 71 indicating a ratio of a tissue included in each pixel as an image relating to tissue areas. With this, in a case where the intermediate image 7 includes the tissue composition ratio image 71, it is possible to easily generate the attenuation coefficient image 9 in which the attenuation coefficient is a value within an appropriate range, based on the ratio of a tissue included in each pixel of the tissue composition ratio image 71.

Further, in this embodiment, as described above, the step for generating the attenuation coefficient image 9 includes a step for assigning an attenuation coefficient to the tissue in the tissue composition ratio image 71, based on a known attenuation coefficient of each tissue area. With this, it is possible to easily generate the attenuation coefficient image 9 in which the attenuation coefficient is a value within an appropriate range, based on the tissue composition ratio image 71 to which the attenuation coefficient is assigned based on known attenuation coefficients.

Further, in this embodiment, as described above, the step of generating the input image 6 includes a step of generating the input image 6 without performing at least one of attenuation correction processing and scatter correction processing. This makes it possible to easily perform the processing for generating the input image 6 by the amount that at least one of attenuation correction processing and scatter correction processing is not performed, as compared with the case where the input image 6 is generated by performing at least one of attenuation correction processing and scatter correction processing.

Further, in this embodiment, as described above, the step of generating the input image 6 includes a step of performing processing including back projection processing on the measurement data 5. With this, an input image 6 can be easily generated by performing processing including back projection processing on the measurement data 5.

Further, in this embodiment, as described above, the input image 6 includes at least one of an image in which image quality conversion processing is not applied to the measurement data 5 on which imaging processing is performed, an image to which image quality conversion processing is applied to the measurement data 5 on which imaging processing is performed, and an image to which the area identification processing is applied. With this, it is possible to generate the intermediate image 7, based on an image in which image quality processing is applied to the measurement data 5 on which imaging processing is performed, and an image to which area identification processing is applied.

Further, in this embodiment, as described above, the step of generating the intermediate image 7 includes a step in which the machine learning model 8 trained in advance is applied to the input image 6. With this, it is possible to easily generate the intermediate image 7 by simply applying the machine learning model 8 trained in advance to the input image 6.

Further, in this embodiment, as described above, the input image 6*a* as training data of the machine learning model 8 includes at least one of a normalized image in which the pixel value range is normalized, an image pixel in which the normalized image is multiplied by a coefficient larger than 0 and smaller than 1, and an image in which a specific area of the normalized image or an image prior to normalization is multiplied by a positive coefficient. With this, it is possible to train the machine learning model 8 by the input images 6*a* with various pixel values. Consequently, it is possible to generate a robust machine learning model 8 against pixel value variations.

Further, in this embodiment, as described above, the machine learning model 8 includes at least one of: a machine learning model 8 in which a three-dimensional image is input; a machine learning model 8 in which an axial cross-sectional image is input; a machine learning model 8 in which a coronal cross-sectional image is input; a machine learning model 8 in which a sagittal cross-sectional image is input; a machine learning model 8 in which a patch image extracted from a three-dimensional image is input; a machine learning model 8 in which a patch image extracted from an axial cross-sectional image is input; a machine learning model 8 in which a patch image extracted from a coronal cross-sectional image is input; and a machine learning model 8 in which a patch image from a sagittal cross-sectional image is input.

With this, it is possible to generate the intermediate image 7 by inputting a three-dimensional image, an axial cross-sectional image, a coronal cross-sectional image, a sagittal cross-sectional image, a patch image extracted from a three-dimensional image, a patch image extracted from an axial cross-sectional image, a patch image extracted from a coronal cross-sectional image, and a patch image extracted from a sagittal cross-sectional image.

Further, in this embodiment, as described above, the machine learning model 8 includes a deep neural network. With this, it is possible to more effectively perform training by a machine learning model 8 including a deep neural network.

Further, in this embodiment, as described above, the deep neural network includes convolution processing. With this, it is possible to more effectively perform training by a deep neural network including convolution processing.

Further, in this embodiment, as described above, the machine learning model 8 is trained using pseudo-reconstructed images 16 generated based on at least one of a Monte Carlo simulation calculation and an analytical simulation calculation. With this, it is possible to generate the machine learning model 8 using the pseudo-reconstructed images 16 generated based on at least one of a Monte Carlo simulation calculation and an analytical simulation calculation. Consequently, there is no need to collect a large number of clinical images, unlike the case where the machine learning model 8 is generated using the actual reconstructed images (clinical images). As a result, it is possible to easily generated the machine learning model 8.

Further, in this embodiment, as described above, the step of generating the attenuation coefficient image 9 includes a step of performing linear combination processing of the tissue composition ratio images 71 of tissues in which known attenuation coefficients are weight coefficients, in a case where the intermediate image 7 includes the tissue composition ratio image 71. With this, in a case where the intermediate image 7 includes the tissue composition ratio image 71, it is possible to easily generate the attenuation coefficient image 9 in which the attenuation coefficient is a value within an appropriate range by performing linear combination processing of the tissue composition ratio images 71 of tissues in which known attenuation coefficients are set to weight coefficients.

Further, in this embodiment, as described above, the measurement data 5 is measurement data of a human head, and the elements constituting an image relating to the tissue area of the intermediate image 7 include at least one of a background, a cavity, a soft tissue, and a bone. With this, in a case where the measurement data 5 is measurement data of a human head, it is possible to easily generate the attenuation coefficient image 9 in which the attenuation coefficient is a value within an appropriate range, from the intermediate image 7 including an image relating to tissue areas.

Further, in this embodiment, as described above, the measurement data 5 is measurement data of a human breast, and the elements constituting an image relating to tissue areas of the intermediate image 7 include at least one of a background and a soft tissue. With this, in a case where the measurement data 5 is measurement data of a human breast, it is possible to easily generate the attenuation coefficient image 9 in which the attenuation coefficient is a value within an appropriate range, from the intermediate image 7 including an image relating to tissue areas.

Further, in this embodiment, as described above, the processing circuit 41 is configured to perform at least one of attenuation correction processing and scatter correction processing based on the attenuation coefficient image 9. With this, it is possible to perform appropriate attenuation correction processing or appropriate scatter correction processing, based on the attenuation coefficient image 9 in which the attenuation coefficient is a value within an appropriate range.

Further, in this embodiment, as described above, a trained model generation method includes: a step of preparing tissue label images 11 indicating a tissue to which each pixel belongs; a step of generating pseudo-radioactivity distribution images 12 and pseudo-attenuation coefficient images 13, based on the tissue label images 11; a step of generating pseudo-measurement data 15 by performing simulation calculations, based on the pseudo-radioactivity distribution images 12 and the pseudo-attenuation coefficient images 13; a step of generating pseudo-reconstructed images 16 by performing imaging processing on the pseudo-measurement data 15; and a step of generating a trained model (machine learning model 8) using the pseudo-reconstructed images 16 as training data.

With this, it possible to generate a trained model (machine learning model 8) using the pseudo-reconstructed images 16 acquired by simulation calculations as training data. Consequently, there is no need to collect a large number of clinical images, unlike the case where the trained model (machine learning model 8) is generated using actual reconstructed images (clinical images) as training data. With this, it is possible to generate a trained model (machine learning model 8) without performing a non-easy task from the viewpoint of protecting personal information, such as, e.g., collecting a large number of clinical images.

(First Modification)

Next, a first modification of the above-described embodiment will be described with reference to FIG. 10. In the first modification of the embodiment, an example is shown in which an intermediate image includes a tissue label image. Note that the same configuration as that of embodiment is denoted by the same reference symbol in the drawings, and the explanation thereof will be omitted.

Figure 10:
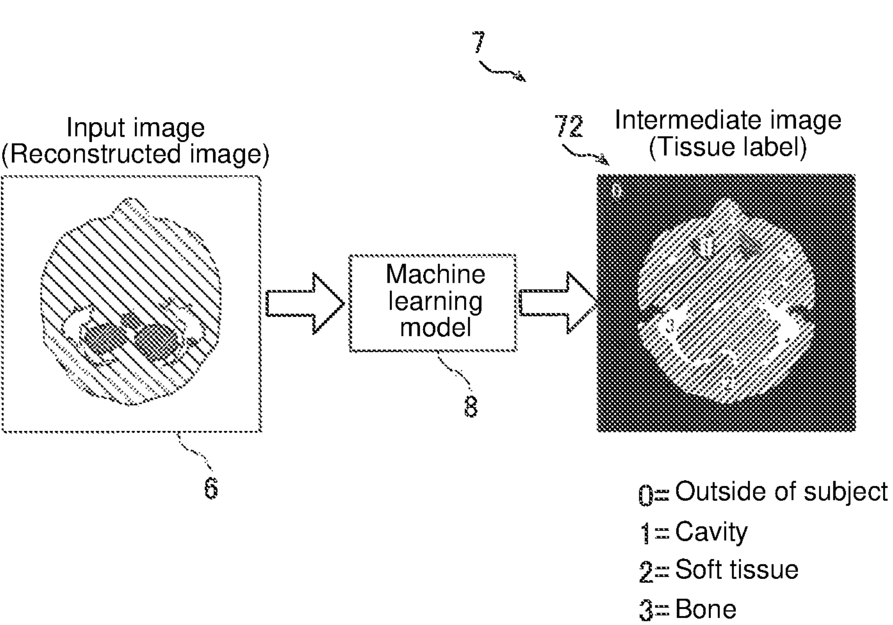
FIG. 10 is a diagram for explaining generation of an intermediate image from an input image according to a first modification of one embodiment.

As shown in FIG. 10, in the first modification of the above-described embodiment, the intermediate image 7 includes a tissue label image 72 indicating a tissue to which each pixel belongs as an image relating to tissue areas. Accordingly, in a case where the intermediate image 7 includes a tissue label image 72, it is possible to easily generate an attenuation coefficient image 9 in which the attenuation coefficient is a value within an appropriate range, based on the tissue to which each pixel of the tissue label image 72 belongs. In the tissue label image 72, in a case where a plurality of tissues is mixed in one pixel, a label is assigned such that the pixel belongs to a tissue occupying the largest ratio.

In the case shown in FIG. 10, the tissue label image 72 is an image of a human head and includes four labels of a background, a cavity, a soft tissue, and a bone. The label area of the background is configured such that the pixel value assigned to the background label is set to a pixel value. Further, the label area of the cavity is configured such that the pixel value assigned to the cavity label is set to a pixel value. Further, the label area of a soft tissue is configured such that the pixel value assigned to a label of a soft tissue is set to a pixel value. Further, the label area of a bone is configured such that the pixel value assigned to the label of a bone is set to a pixel value. Note that four labels are assigned by pixel values (integer values) different from each other.

In the first modification of the above-described embodiment, in Step 104 of the above-described embodiment, the attenuation coefficient image 9 is generated based on the tissue label image 72 of the intermediate image 7 and known attenuation coefficients of tissue areas. Specifically, an attenuation coefficient is assigned to a tissue in the label image 72 based on known attenuation coefficients. With this, it is possible to easily generate an attenuation coefficient image 9 in which the attenuation coefficient is a value within an appropriate range, based on the tissue label image 72 in which an attenuation coefficient is assigned based on known attenuation coefficients. More specifically, assignment processing of a known attenuation coefficient corresponding to a label value of a tissue label image 72 is performed. With this, in a case where the intermediate image 7 includes a tissue label image 72, it is possible to easily generate an attenuation coefficient image 9 in which the attenuation coefficient is a value within an appropriate range by performing assignment processing of a known attenuation coefficient corresponding to a label value of a tissue label image 72.

In the first modification of the embodiment, assignment processing of a known attenuation coefficient corresponding to a label value of the tissue label image 72 is performed according to the following Expression (3).

$$\mu_j = \mu^*_{l_j} \tag{3}$$

where, j: Pixel number $l_j$: Label value (tissue number) of pixel j $\mu_j$: Attenuation coefficient of pixel j $\mu^*_l$: Attenuation coefficient (known attenuation coefficient) of label value l For example, in a case where the tissue label image 72 is an image of a human head and includes four labels of a background, a cavity, a soft tissue, and a bone, the following processing is performed. That is, by using an attenuation coefficient $\mu^*_0$ of a background, an attenuation coefficient $\mu^*_1$ of a cavity, an attenuation coefficient $\mu^*_2$ of a soft tissue, and an attenuation coefficient $\mu^*_3$ of a bone, which are generally known, assignment processing of a known attenuation coefficient corresponding to a label value of a tissue label image 72 is performed according to the above-described Formula (3).

Further, the machine learning model 8 configured to output a tissue label image 72, basically, does not directly output a tissue label image 72 but outputs certainty degree for each pixel as an intermediate output. The certainty degree is an index that may have a stochastic implication for determining that a pixel belongs to which label. Then, the machine learning model 8 configured to output the tissue label image 72 finally outputs the tissue label image 72 such that it belongs to the pixel in which the acquired certainty degree is maximum. Here, the certainty degree may be a value of 0 to 1, and the sum of the certainty degree of all labels may be set to 1. For this reason, it is possible to generate an attenuation coefficient image 9 by performing linear combination processing in the same manner as in the tissue composition ratio image 71 of the above-described embodiment by replacing the tissue composition ratio in the above-described embodiment with certainty degree. That is, the attenuation coefficient image 9 may be generated by performing linear combination processing of certainty degree images, which are intermediate output of the tissue label image 72, using known attenuation coefficients as weight coefficients. Thus, in a case where the intermediate image 7 includes a tissue label image 72, it is possible to easily and accurately generate an attenuation coefficient image 9 in which the attenuation coefficient is a value within an appropriate range, by performing linear combination processing of certainty degree images, which are an intermediate output of the tissue label image 72, in which known attenuation coefficients are set to weight coefficients.

Further, in the first modification of the embodiment, in Step 115 of the above-described embodiment, by assuming a pixel size of the same low resolution as the pseudo-reconstructed image 16, calculating the ratio (composition ratio) of each tissue included in one pixel with respect to a tissue label image 14 of a high resolution, and assigning a label such that a pixel belongs to a tissue occupying the maximum ratio, an intermediate image 7*a* as a tissue composition ratio image is generated.

(Second Modification)

Next, a second modification of the above-described embodiment will be described with reference to FIG. 11 and FIG. 12. In the second modification of the above-described embodiment, an example will be explained in which a plurality of machine learning models is combined. Note that the same configuration as that of the above-described embodiment is denoted by the same reference symbol in the drawings, and the explanation thereof will be omitted.

Figure 11:
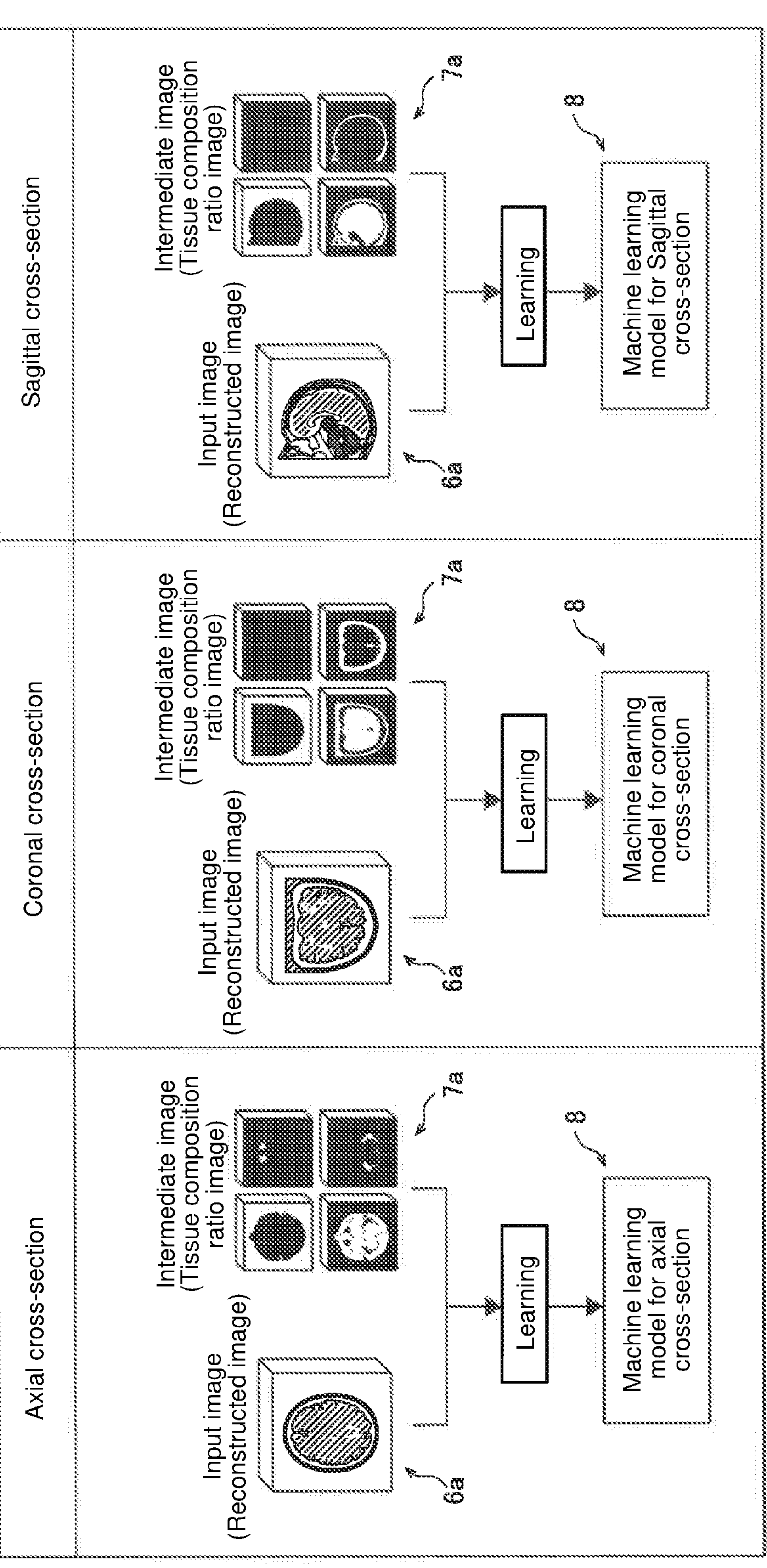
FIG. 11 is a diagram for explaining a machine learning model according to a second modification of one embodiment.

As shown in FIG. 11, in the second modification of the above-described embodiment, the machine learning model 8 includes three machine learning models, i.e., a machine learning model for axial cross-section, a machine learning model for coronal cross-section, and a machine learning model for sagittal cross-section. The machine learning model for axial cross-section is trained using input images 6*a*, which are axial cross-sectional images, as inputs and intermediate images 7*a* corresponding to the axial cross-sectional image as training images. The machine learning model for coronal cross-section is trained using coronal cross-sectional images of input images 6*a* as inputs and intermediate images 7*a* corresponding to the coronal cross-sectional images as training images. The machine learning model for sagittal cross-section is trained using input images 6*a*, which are sagittal cross-sectional images, as inputs and intermediate images 7*a* corresponding to the sagittal cross-sectional images as training images.

Further, in the second modification of the above-described embodiment, as shown in FIG. 12, in Step 102 of the above-described embodiment, three input images 6, i.e., an axial cross-sectional image, a coronal cross-sectional image, and a sagittal cross-sectional image, are generated.

In the second modification of the above-described embodiment, in Step 103 of the above-described embodiment, three intermediate images 7, i.e., a tissue composition ratio image corresponding to the axial cross-sectional image, a tissue composition ratio image corresponding to the coronal cross-sectional image, and a tissue composition ratio image corresponding to the sagittal cross-sectional image, are generated.

In the second modification of the above-described embodiment, in Step 104 of the above-described embodiment, an attenuation coefficient image 9 is generated based on three intermediate images 7, i.e., a tissue composition ratio image corresponding to an axial cross-sectional image, a tissue composition ratio image corresponding to a coronal cross-sectional image, and a tissue composition ratio image corresponding to a sagittal cross-sectional image. Specifically, cross-sectional transform processing is performed such that any two of the tissue composition ratio image corresponding to the axial cross-sectional image, the tissue composition ratio image corresponding to the coronal cross-sectional image, and the tissue composition ratio image corresponding to the sagittal cross-sectional image become an image corresponding to the remaining one cross-section. Then, an average image (average tissue composition ratio image) of three tissue composition ratio images having the same cross-section is generated. At this time, simple averaging processing may be performed, or weighted averaging processing may be performed in which a highly accurate cross-section is multiplied by a weight. Then, in the same manner as in the above-described embodiment, the average tissue composition ratio image is subjected to linear combination processing, thereby generating an attenuation coefficient image 9.

(First and Second modifications of Second Modification)

Next, with reference to FIG. 13 and FIG. 14, first and second modifications of the second modification of the above-described embodiment will be described. In the first and second modifications of the second modification of the above-described embodiment, an example will be described in which an intermediate image includes a tissue label image in the second modification. Note that the same configuration as that of the above-described embodiment is denoted by the same reference symbol in the drawings, and the explanation thereof will be omitted.

Figure 13:
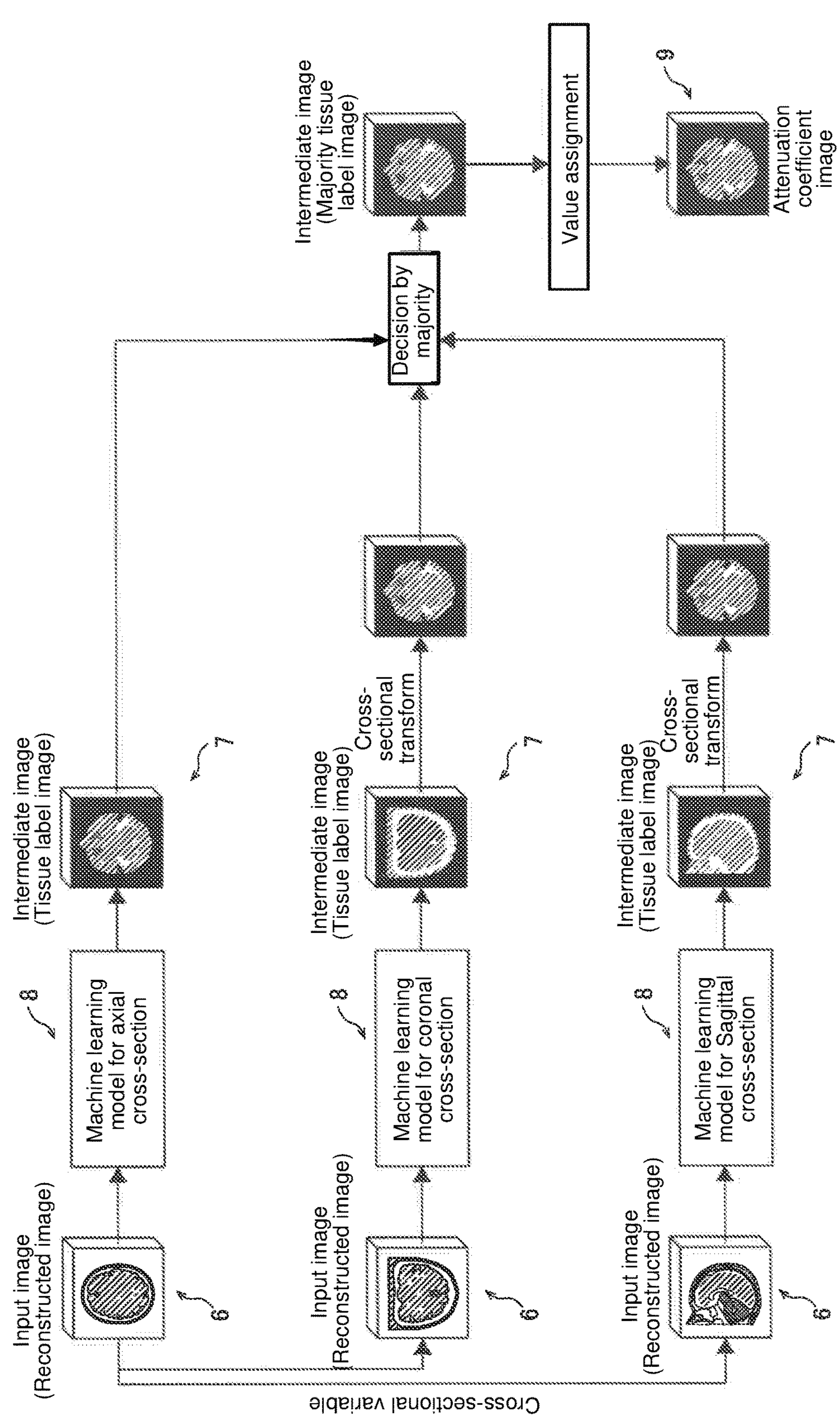
FIG. 13 is a diagram for explaining generation of an attenuation coefficient image from an intermediate image according to a first modification of the second modification of one embodiment.
Figure 14:
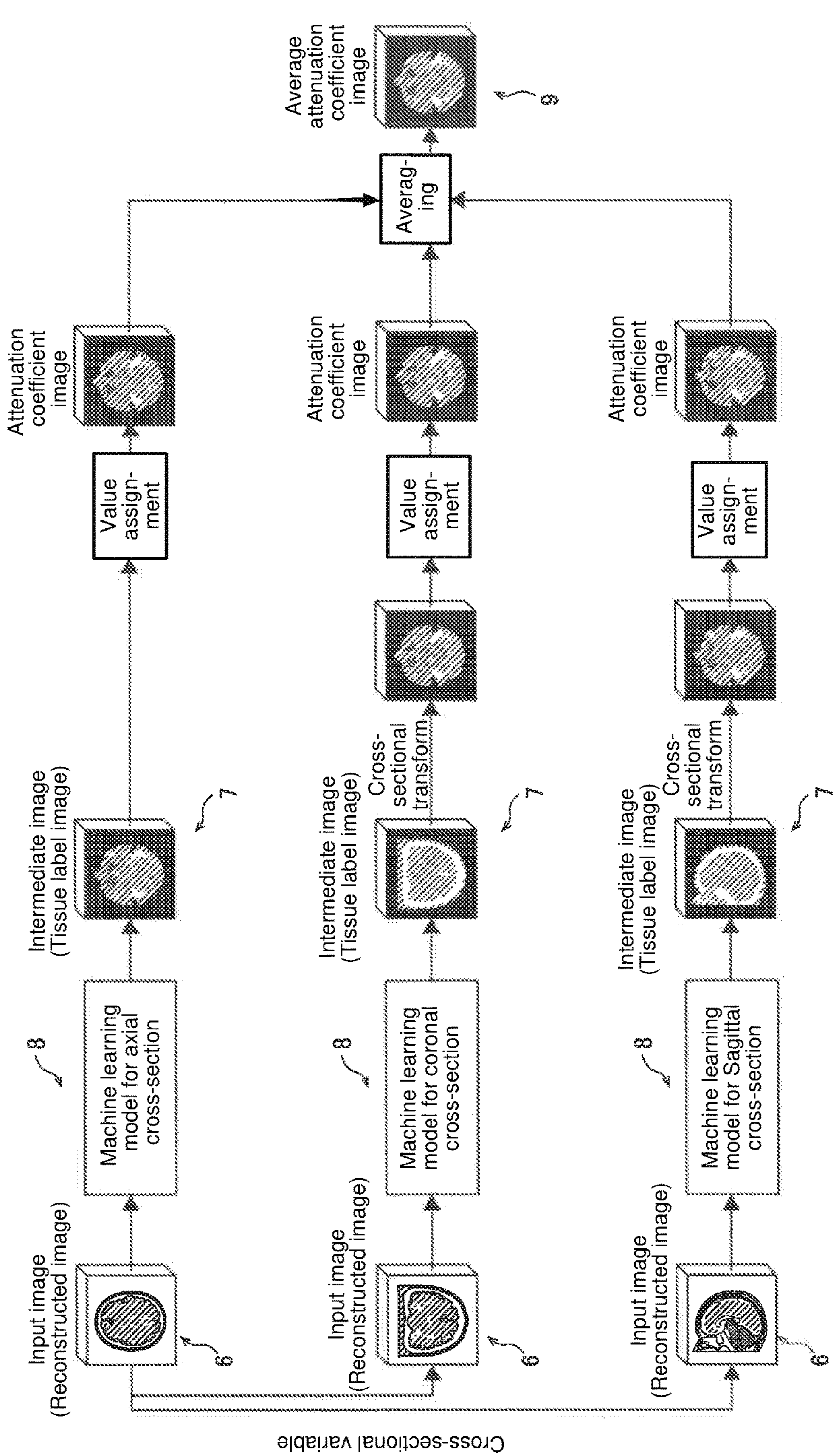
FIG. 14 is a diagram for explaining generation of an attenuation coefficient image from an intermediate image according to a second modification of the second modification of one embodiment.

As shown in FIG. 13, in the first modification of the second modification of the above-described embodiment, in Step 103 of the above-described embodiment, three intermediate images 7, i.e., a tissue label image corresponding to an axial cross-sectional image, a tissue label image corresponding to a coronal cross-sectional image, and a tissue label image corresponding to a sagittal cross-sectional image.

Then, in the first modification of the second modification of the above-described embodiment, in Step 104 of the above-described embodiment, an attenuation coefficient image 9 is generated based on three intermediate images 7, i.e., a tissue label image corresponding to an axial cross-sectional image, a tissue label image corresponding to a coronal cross-sectional image, and a tissue label image corresponding to a sagittal cross-sectional image. Specifically, cross-sectional transform processing is performed such that any two of the tissue label image corresponding to an axial cross-sectional image, the tissue label image corresponding to a coronal cross-sectional image, and the tissue label image corresponding to a sagittal cross-sectional image become an image corresponding to the remaining one cross-section. Then, a majority image (majority tissue label image) in which the label value of each pixel is determined by the majority decision of three tissue label images having same cross-section. At this time, in a case where the label value cannot be determined by a majority decision, a label value of a predetermined cross-section may be adopted. In the same manner as in the first modification of the above-described embodiment, an attenuation coefficient image 9 is generated by performing assignment processing of the majority decision tissue label image.

The attenuation coefficient image 9 may be generated by a method other than a majority decision method. Specifically, as shown in FIG. 14, in a second modification of the second modification of the above-described embodiment, unlike the first modification of the second modification of the above-described embodiment, three attenuation coefficient images are generated so as to correspond to each of the three tissue label images having same cross-section. Then, an attenuation coefficient image as an average image of the three attenuation coefficient images is generated as a final attenuation coefficient image 9.

(Third Modification)

Next, a third modification of the above-described embodiment will be described with reference to FIG. 15. In the third modification of the above-described embodiment, an example is described in which a plurality of types of inputs (input image multi-channelization) are performed on a machine learning model. Note that the same configuration as that of the above-described embodiment is denoted by the same reference symbol in the drawings, and the explanation thereof will be omitted.

Figure 15:
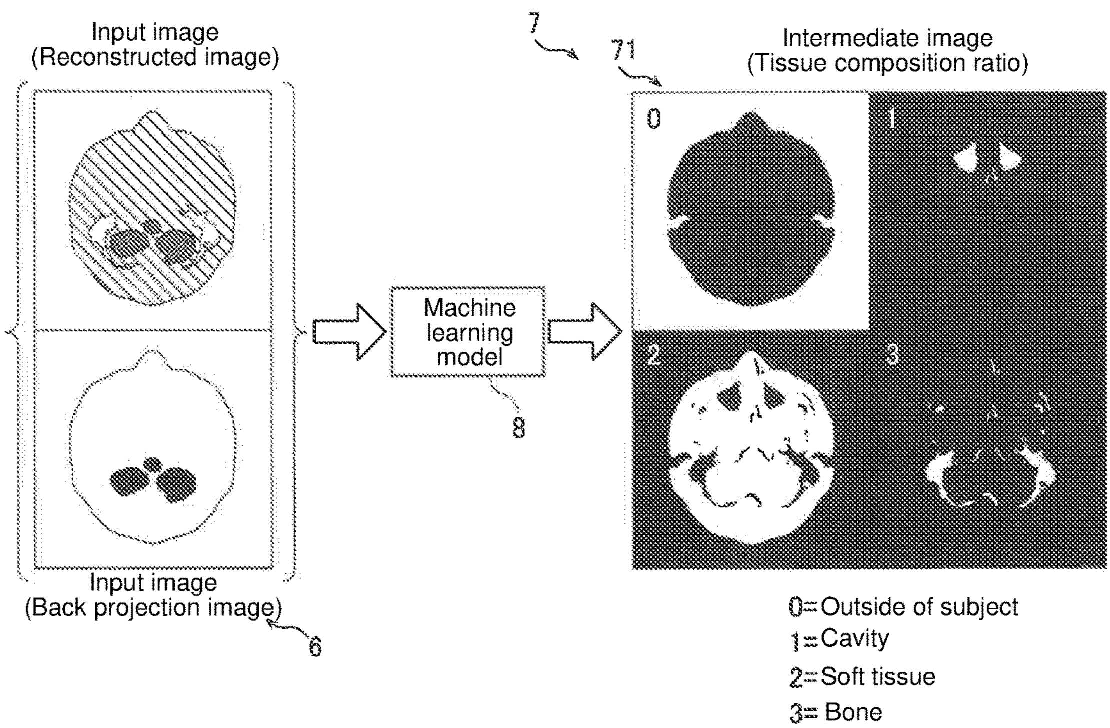
FIG. 15 is a diagram for explaining generation of an intermediate image from an input image according to a third modification of one embodiment.

As shown in FIG. 15, in the third modification of the above-described embodiment, two types of input images 6, i.e., a reconstructed image generated by performing reconstruction processing and a back projection image generated by performing simple back projection processing, are input to the machine learning model 8. In the third modification of the above-described embodiment, the machine learning model 8 outputs a tissue composition ratio image 71 of the intermediate image 7 based on the two types of input images 6.

Note that the combination of input images 6 is not limited to the combination of a reconstructed image generated by performing reconstruction processing and a back projection image generated by performing simple back projection processing. For example, the combination of input images 6 may be a combination of a plurality of types of reconstructed images in which reconstruction algorithms differ from each other. Further, for example, the combination of input images 6 may be a combination of a plurality of types of reconstructed images in which iteration numbers of iterative image reconstruction differ from each other. Further, for example, the combination of the input images 6 may be a combination of a plurality of types of reconstructed images having resolutions different from each other. In this case, the input images 6 include images of two or more types of resolutions. As a result, it is possible to generate an intermediate image 7 based on input images 6 of various types of resolutions, as compared with the case where the input image 6 includes only one type of resolution. The combination of the input images 6 may be a combination of a plurality of types of reconstructed images on which image processing different from each other is performed. The combination of the input images 6 may be a combination of these images.

(First to Fourth Modifications of Third Modification)

Next, first to fourth modifications of the third modification of the above-described embodiment will be described with reference to FIG. 16 to FIG. 19. In the first to third modifications of the above-described embodiment, an example will be described in which a reconstructed image and information other than the reconstructed image and the back projection image are combined in the third modification. Note that the same configuration as that of the above-described embodiment is denoted by the same reference symbol in the drawings, and the explanation thereof will be omitted.

Figure 16:
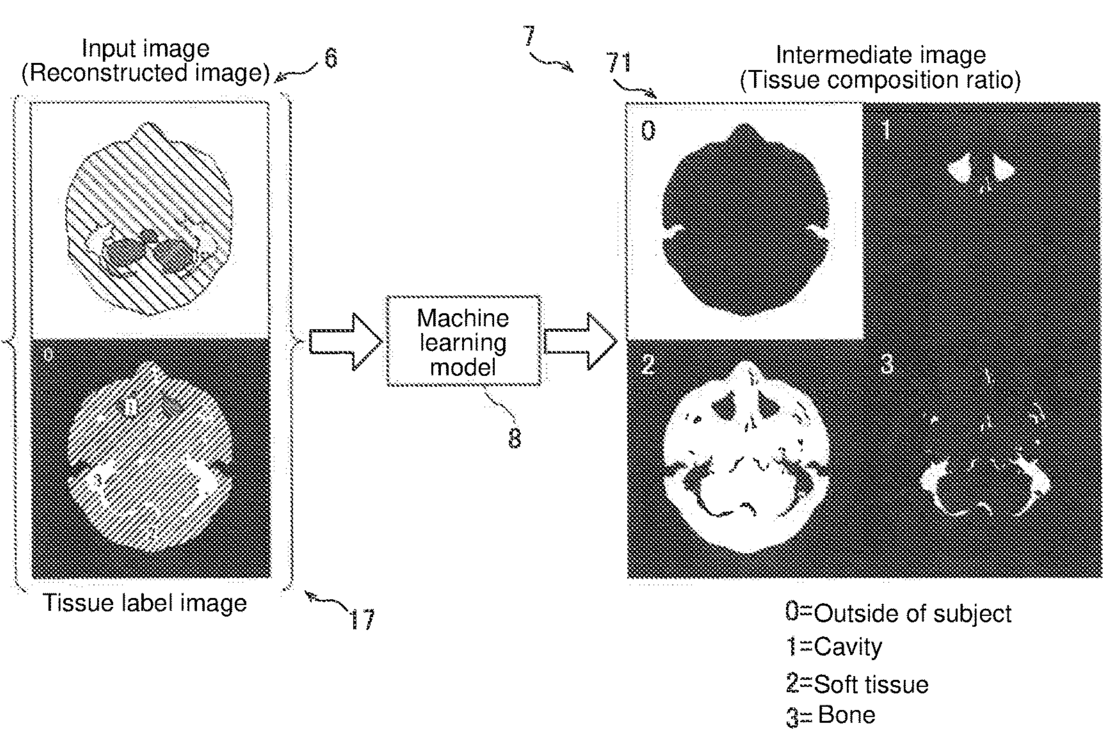
FIG. 16 is a diagram for explaining generation of an intermediate image from an input image according to a first modification of the third modification of one embodiment.

As shown in FIG. 16, in the first modification of the third modification of the above-described embodiment, two types of images, i.e., an input image (reconstructed image) 6 and a tissue label image 17 indicating the tissues to which the respective pixels belong, are input to a machine learning model 8. In the first modification of the third modification of the above-described embodiment, the machine learning model 8 outputs a tissue composition ratio image 71 of the intermediate image 7 based on the input image 6 and the tissue label image 17 as auxiliary information.

Figure 17:
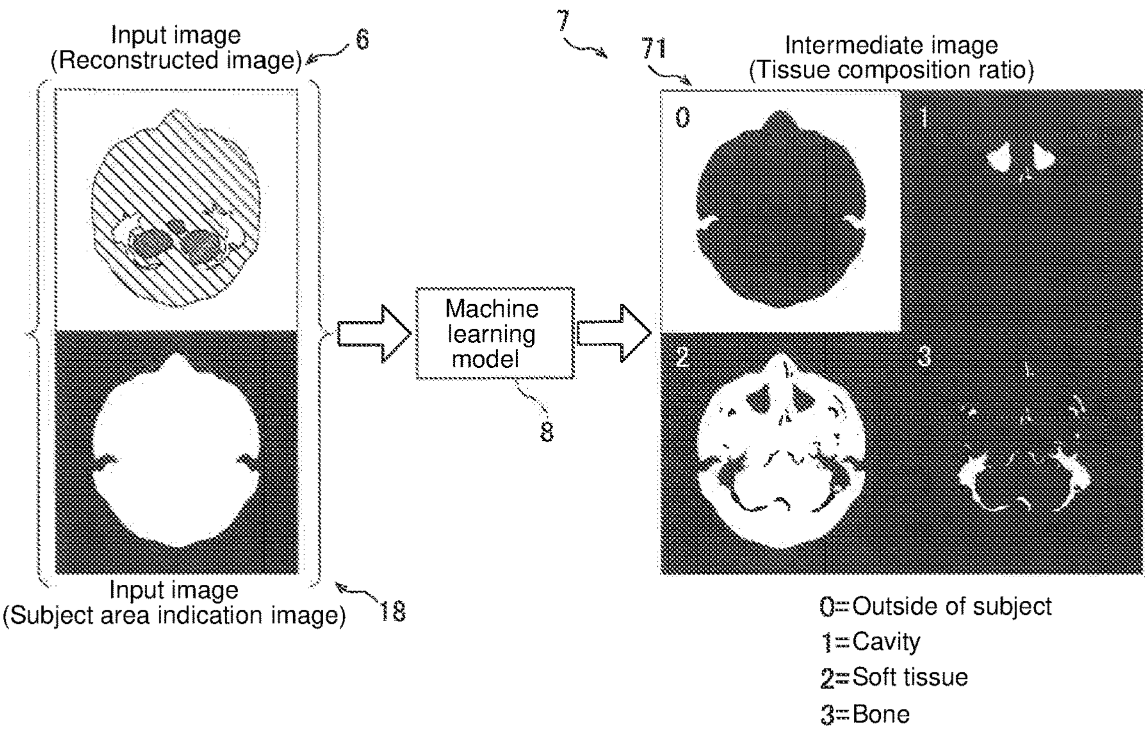
FIG. 17 is a diagram for explaining generation of an intermediate image from an input image according to a second modification of the third modification of one embodiment.

As shown in FIG. 17, in the second modification of the third modification of the above-described embodiment, two types of images, i.e., an input image (reconstructed image) 6 and a subject area indication image 18 indicating the area of the subject 100 are input to the machine learning model 8. In the second modification of the third modification of the above-described embodiment, the machine learning model 8 outputs a tissue composition ratio image 71 of an intermediate image 7 based on the input image 6 and the subject area indication image 18 as auxiliary information. Further, a single tissue area indication image indicating a single tissue area may be used instead of the subject area indication image 18.

Figure 18:
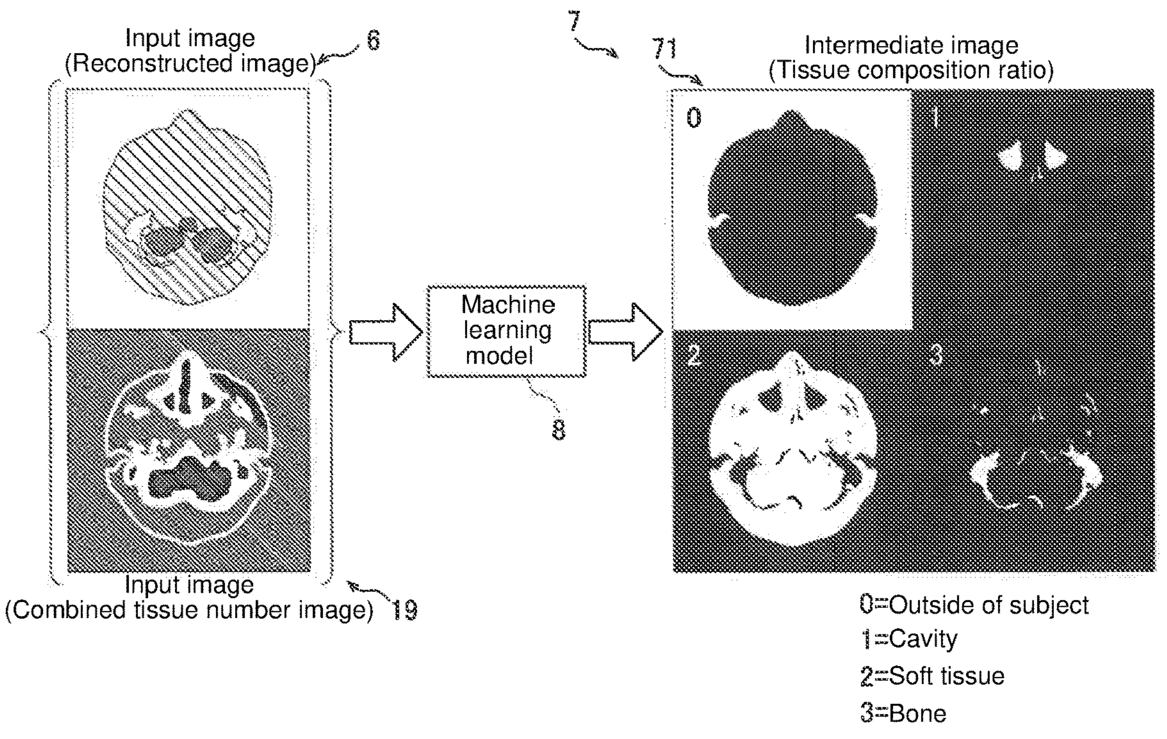
FIG. 18 is a diagram for explaining generation of an intermediate image from an input image according to a third modification of the third modification of one embodiment.

Further, as shown in FIG. 18, in the third modification of the third modification of the above-described embodiment, two types of images, i.e., an input image (reconstructed image) 6 and a combined tissue number image 19 indicating the number of types of tissues included in a pixel are input to the machine learning model 8. In the third modification of the third modification of the above-described embodiment, the machine learning model 8 outputs a tissue composition ratio image 71 of an intermediate image 7 based on the input image 6 and the combined tissue number image 19 as auxiliary information.

Figure 19:
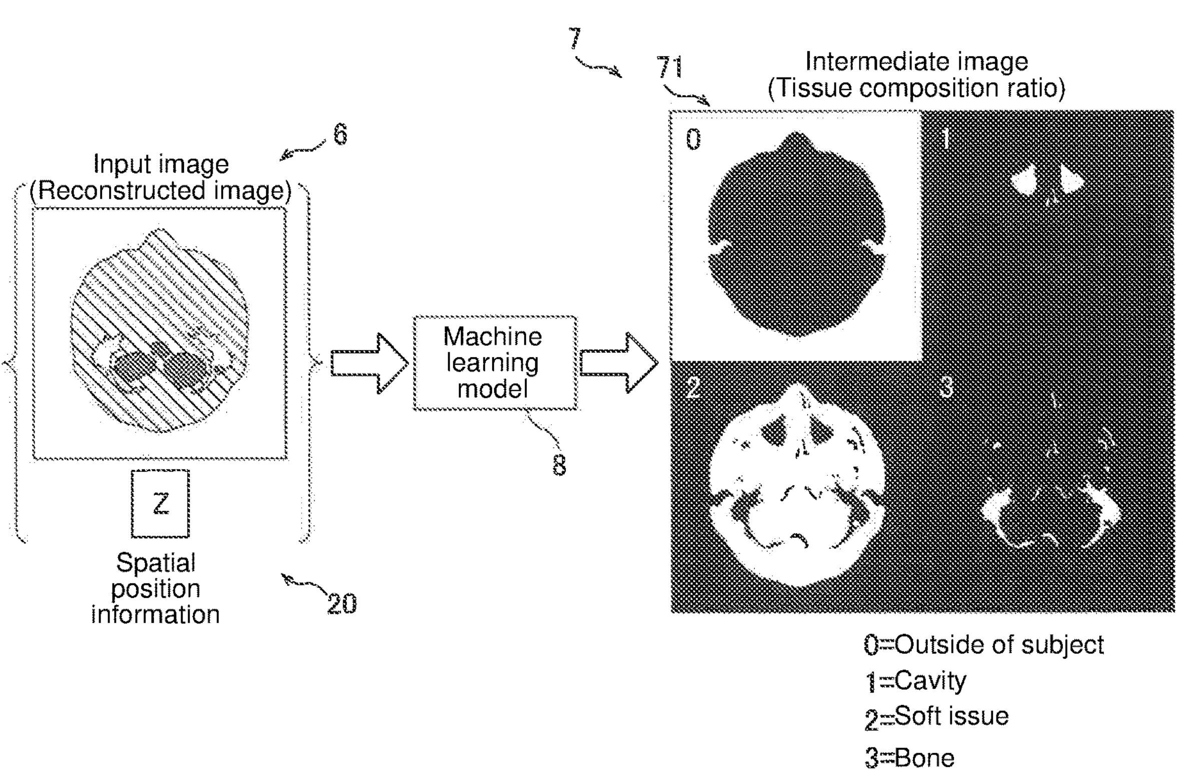
FIG. 19 is a diagram for explaining generation of an intermediate image from an input image according to a fourth modification of the third modification of one embodiment.

Further, as shown in FIG. 19, in the fourth modification of the third modification of the above-described embodiment, two types of images, i.e., an input image (reconstructed image) 6 and information relating to a spatial position of the input image 6, which is non-image information, are input to the machine learning model 8. That is, in the fourth modification of the third modification of the above-described embodiment, the machine learning model 8 receives, in addition to the input image 6, information 20 relating to the spatial position of the input image 6 as an input. As a result, the intermediate image 7 can be effectively generated using not only the input image 6 but also the information 20 relating to the spatial position of the input image 6. As the information 20 relating to the spatial position of the input image 6, for example, the distance and the relative distance from the center of gravity of the subject can be adopted. In the fourth modification of the third modification of the above-described embodiment, the machine learning model 8 outputs a tissue composition ratio image 71 of an intermediate image 7 based on the input image 6 and the information 20 relating to the spatial position of the input image 6 as auxiliary information.

(Fourth Modification)

Next, with reference to FIG. 20, a fourth modification of the above-described embodiment will be described. In the fourth modification of the above-described embodiment, an example is described in which a plurality of types of images is output from the machine learning model. Note that the same configuration as that of the above-described embodiment is denoted by the same reference symbol in the drawings, and the explanation thereof will be omitted.

Figure 20:
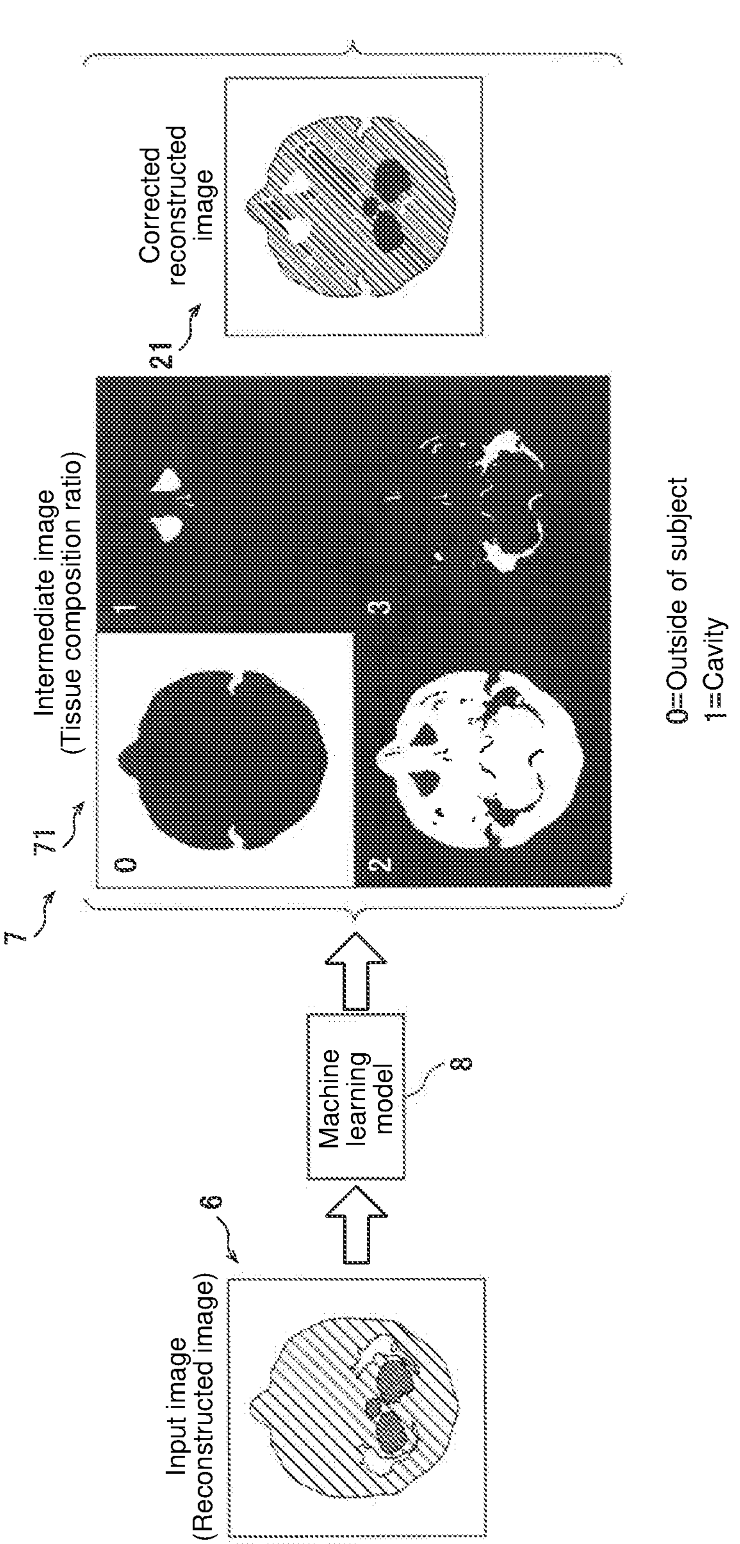
FIG. 20 is a diagram for explaining generation of an intermediate image and a reconstructed image with an attenuation correction from an input image according to a fourth modification of one embodiment.

As shown in FIG. 20, in the fourth modification of the above-described embodiment, the machine learning model 8 outputs two types of images, i.e., an intermediate image 7 including a tissue composition ratio image 71 and a reconstructed image 21 to which at least one of attenuation correction processing and scatter correction processing is applied. In the fourth modification of the above-described embodiment, the machine learning model 8 simultaneously outputs a reconstructed image 21 to which at least one of attenuation correction processing and scatter correction processing is applied, in addition to the intermediate image 7. With this, it is possible to generate not only the intermediate image 7 but also the reconstructed image 21 to which at least one of attenuation correction processing and scatter correction processing is applied, by simply applying a machine learning model 8 trained in advance to the input image 6. In the fourth modification of the above-described embodiment, for example, the machine learning model 8 outputs the intermediate image 7 and the reconstructed image 21 to which attenuation correction processing is applied.

Further, in the fourth modification of the above-described embodiment, the machine learning model 8 includes a multi-output type (multi-task type) deep convolutional neural network for outputting two types of images, i.e., the intermediate image 7 and the reconstructed image 21.

(Fifth Modification)

Next, with reference to FIG. 21 and FIG. 22, a fifth modification of embodiment will be described. In the fifth modification of the above-described embodiment, an example is described in which a plurality of machine learning models each corresponding to each tissue of a tissue composition ratio image is combined. Note that the same configuration as that of the above-described embodiment is denoted by the same reference symbol in the drawings, and the explanation thereof will be omitted.

Figure 21:
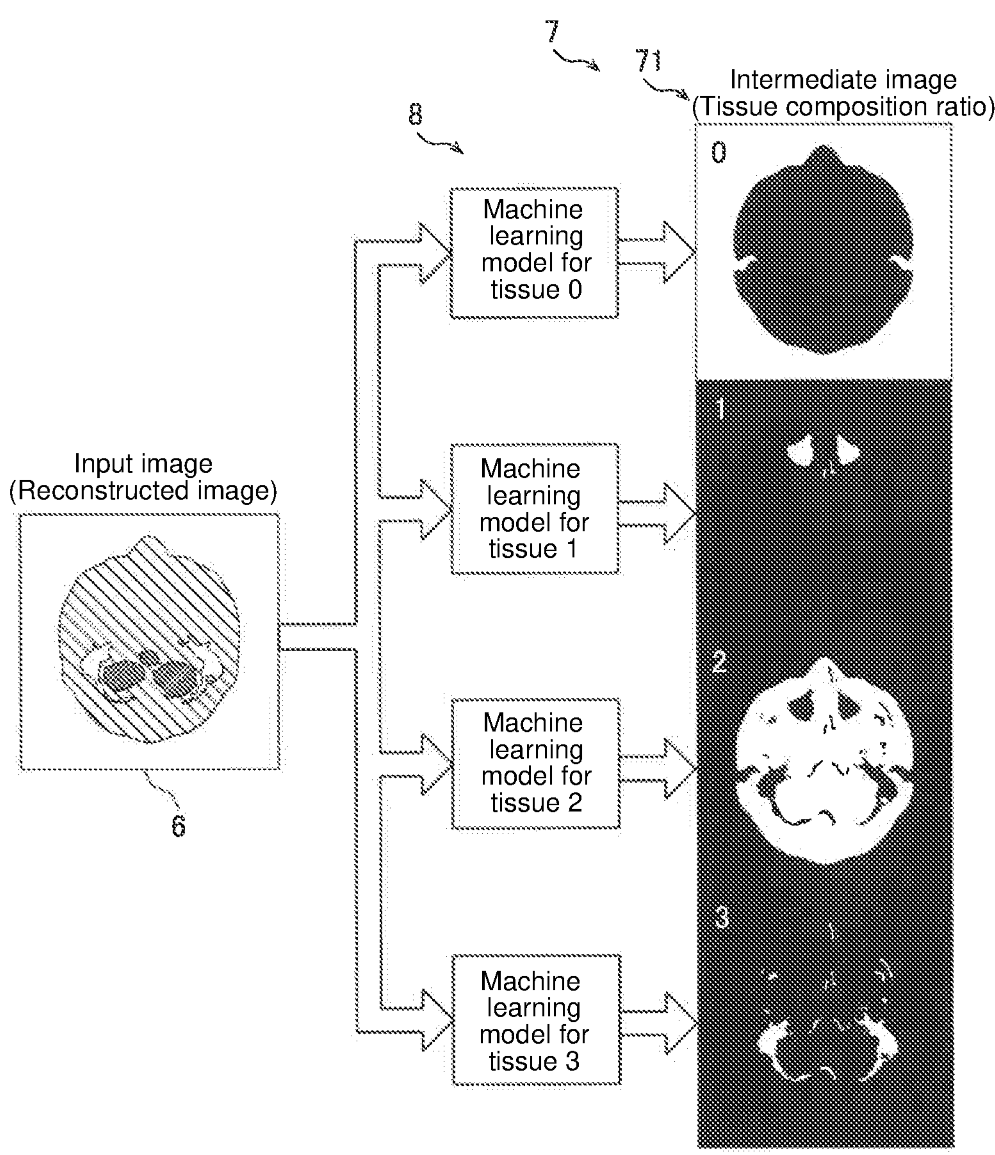
FIG. 21 is a diagram for explaining generation of an intermediate image from an input image according to a fifth modification of one embodiment.

As shown in FIG. 21, in the fifth modification of the above-described embodiment, the machine learning model 8 includes a plurality of machine learning models each corresponding to each tissue of the tissue composition ratio image 71 of the intermediate image 7. In the example shown in FIG. 21, the tissue composition ratio image 71 is an image of a human head. The machine learning model 8 includes four machine learning models, i.e., a machine learning model for a background, a machine learning model for a cavity, machine learning model for a soft tissue, and a machine learning model for a bone. In the machine learning model for a background, an input image 6 is input, and a tissue composition ratio image 71 corresponding to the background is output. In the machine learning model for a cavity, an input image 6 is input, and a tissue composition ratio image 71 corresponding to the cavity is output. In the machine learning model for a soft tissue, an input image 6 is input, and a tissue composition ratio image 71 corresponding to the soft tissue is output. In the machine learning model for a bone, an input image 6 is input, and a tissue composition ratio image 71 corresponding to the bone is output.

Figure 22:
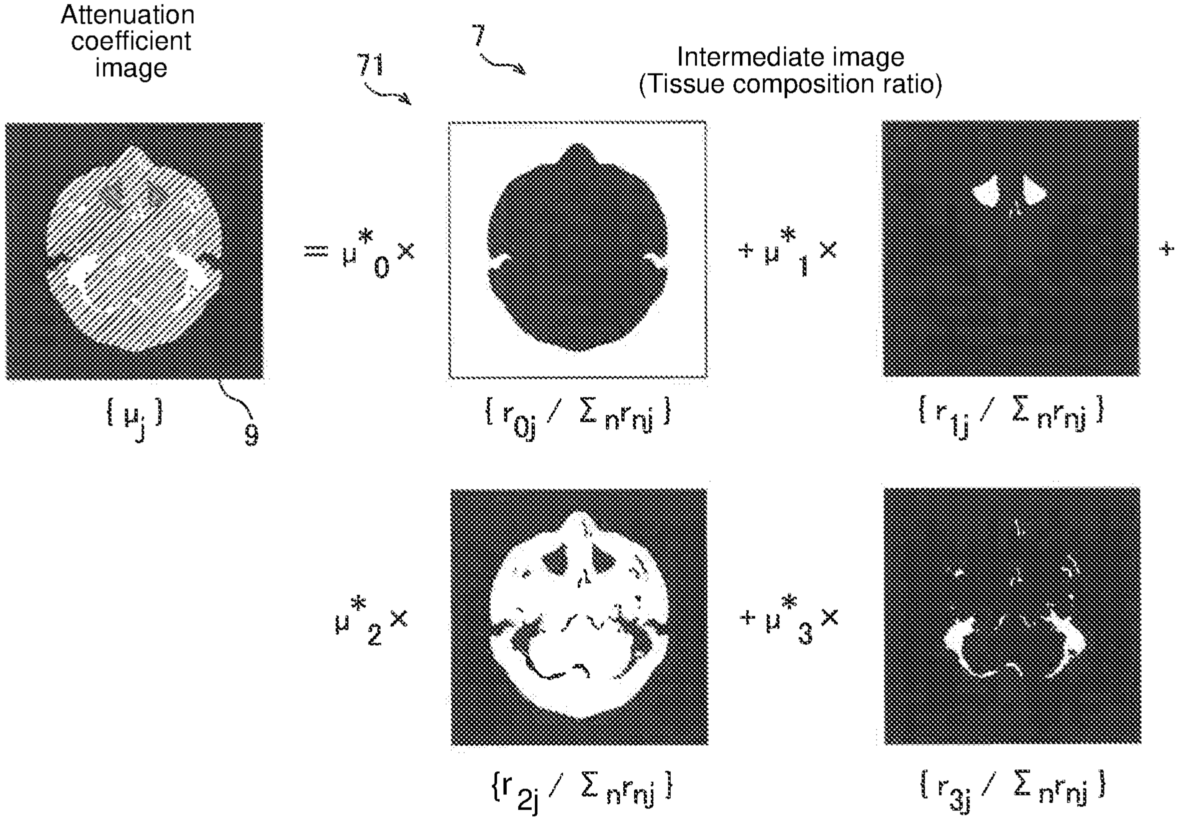
FIG. 22 is a diagram for explaining generation of an attenuation coefficient image from an intermediate image according to a fifth modification of one embodiment.

Further, in the fifth modification of the above-described embodiment, as shown in FIG. 22, linear combination processing of the tissue composition ratio images 71 of tissues using known attenuation coefficients as weight coefficients is performed by the following Formula (4).

$$\mu_j = \frac{\sum_{n=1}^{N} \mu_n^* r_{nj}}{\sum_{n=i}^{N} r_{nj}} \tag{4}$$

where, n: Tissue number j: Pixel number $\mu_j$: Attenuation coefficient for pixel j $\mu^*_n$: Attenuation coefficient (known attenuation coefficient) of tissue n $r_{nj}$: Composition ratio ($0 \le r_{nj} \le 1$) of tissue n of pixel j In the fifth modification of the above-described embodiment, the tissue composition ratio image 71 of each tissue is generated by mutually independent machine learning models, and therefore, unlike the above-described embodiment, the condition that the sum of composition ratios is 1 is not automatically satisfied. Therefore, in the fifth modification of the above-described embodiment, as shown in Formula (4), normalization processing (processing of dividing by the denominator term of Expression (4)) is performed at the time of linear combination processing.

(Sixth Modification)

Next, with reference to FIG. 23, a sixth modification of the above-described embodiment will be described. In the sixth modification of the above-described embodiment, an example is described in which one machine learning model processes images having cross-sections different from each other. Note that the same configuration as that of the above-described embodiment is denoted by the same reference symbol in the drawings, and the explanation thereof will be omitted.

As shown in FIG. 23, in the sixth modification of the above-described embodiment, the machine learning model 8 includes a deep neural network for an axial cross-section, a deep neural network for a coronal cross-section, and a deep neural network for a sagittal cross-section. In the deep neural network for the axial cross-section, an input image 6, which is a three-dimensional axial cross-sectional image, is input, and a tissue composition ratio image corresponding to an axial cross-sectional image is output. In the deep neural network for a coronal cross-section, an input image 6, which is a three-dimensional coronal cross-sectional image, is input, and the tissue composition ratio image corresponding to a coronal cross-sectional image is output. In the deep neural network for a sagittal cross-section, an input image 6, which is a three-dimensional sagittal cross-sectional image, is input, and a tissue composition ratio image corresponding to a sagittal cross-sectional image is output.

Further, in the sixth modification of the above-described embodiment, the machine learning model 8 is configured to perform cross-sectional transform processing such that any two of a tissue composition ratio image corresponding to an axial cross-sectional image, a tissue composition ratio image corresponding to a coronal cross-sectional image, and a tissue composition ratio image corresponding to a sagittal cross-sectional image become images corresponding to the remaining one cross-section. Further, in the sixth modification of the above-described embodiment, the machine learning model 8 includes a deep neural network in which three tissue composition ratio images having same cross-section are input, and three-dimensional tissue composition ratio image corresponding to the three tissue composition ratio images having same cross-section is output. With this, in the sixth modification of the above-described embodiment, an intermediate image 7 is generated as a three-dimensional tissue composition ratio image.

Modified Embodiment

It should be understood that the embodiments disclosed here are examples in all respects and are not restrictive. The scope of the present invention is indicated by the appended claims rather than by the description of the above-described embodiments and includes all modifications (changes) within the meanings and the scopes equivalent to the claims.

For example, in the above-described embodiments, among the configurations described in the above-described embodiment and the first to sixth modifications, configurations applicable to each other can be combined as appropriate.

Further, in the above-described embodiments, an example is shown in which the nuclear medicine diagnostic apparatus is a PET device, but the present invention is not limited thereto. For example, the nuclear medicine diagnostic apparatus may be a SPECT (Single Photon Emission Computed Tomography) device other than a PET device.

Further, in the above-described embodiments, an example is shown in which normalization processing for normalizing the pixel value range to [0, 1] is performed on a pseudo-reconstructed image, but the present invention is not limited thereto. In the present invention, the normalized range may be any range, such as [−1, 1] other than [0, 1].

Further, in the above-described embodiments, an example is shown in which a machine learning model is trained using pseudo images prepared based on simulation calculations, but the present invention is not limited thereto. In the present invention, the machine learning model may have been learned using both pseudo images and real images (real subject images). With this, the machine learning model can be trained using various data. As a consequence, it is possible to generate a robust machine learning model against variations of subjects. Further, the machine learning model may be additionally trained using real images with the machine learning model trained with pseudo images as a base model. With this, even in a case where the machine learning model is trained using both the pseudo images and the real images, it is possible to effectively train the machine learning model.

Further, in the above-described embodiments, an example is shown in which an input image is generated without performing at least one of attenuation correction processing and scatter correction processing, but the present invention is not limited thereto. In the present invention, an input image in which both attenuation correction processing and scatter correction processing are performed may be generated.

In the above-described embodiments, an example is shown in which linear combination processing of tissue composition ratio images of tissues using known attenuation coefficients as weight coefficients is performed to generate an attenuation coefficient image, but the present invention is not limited thereto. In the present invention, in a case where an attenuation coefficient image is generated from a tissue composition ratio image, an attenuation coefficient image may be generated by performing assignment processing of a known attenuation coefficient corresponding to a tissue having the largest tissue composition ratio.

Further, in the second modification of the above-described embodiment, an example is shown in which the machine learning model includes three machine learning model, i.e., a machine learning model for axial cross-section, a machine learning model for coronal cross-section, and a machine learning model for sagittal cross-section, but the present invention is not limited thereto. In the present invention, the machine learning model may include any two of a machine learning model for axial cross-section, a machine learning model for coronal cross-section, and a machine learning model for sagittal cross-section.

Further, in the fourth modification of the above-described embodiment, an example is shown in which two types of images, i.e., an intermediate image and a reconstructed image, are output from the machine learning model, but the present invention is not limited thereto. In the present invention, three or more types of images may be output from the machine learning model. Further, an intermediate image and an image other than a reconstructed image may be output from the machine learning model. For example, an intermediate image and a combined tissue number image indicating the number of types of tissues included in a pixel may be output from the machine learning model.

Further, in the above-described embodiments, for convenience of explanation, each processing of a processing circuit is described using a "flow-driven" flowchart, but the present invention is not limited thereto. In the present invention, the above-described each processing may be performed by an "event-driven type" which is executed on an event-by-event basis. In this case, the processing may be performed in a complete event-driven fashion or in combination of event-driven type processing and flow-driven type processing.

[Aspects]

It will be understood by those skilled in the art that the above-described exemplary embodiments are concrete examples of the following aspects.

(Item 1)

An attenuation coefficient image generation method for a nuclear medicine diagnostic apparatus, the method being configured to generate an attenuation coefficient image of a subject, the method comprising the steps of:

generating an input image by performing imaging processing on measurement data acquired based on detection of radiation emitted from the subject;

generating an intermediate image including an image relating to tissue areas based on the input image; and generating an attenuation coefficient image based on the intermediate image and known attenuation coefficients of the tissue areas (Item 2)

The attenuation coefficient image generation method as recited in the above-described Item 1, wherein the intermediate image includes, as an image relating to the tissue area, at least one of a tissue composition ratio image indicating a ratio of a tissue included in each pixel and a tissue label image indicating a tissue to which each pixel belongs.

(Item 3)

The attenuation coefficient image generation method as recited in the above-described Item 2, wherein the step of generating the attenuation coefficient image includes a step of assigning an attenuation coefficient to a tissue in the tissue composition ratio image or a tissue in the tissue label image, based on known attenuation coefficients.

(Item 4)

The attenuation coefficient image generation method as recited in the above-described Item 1, wherein the step of generating the input image includes a step of generating the input image without performing at least one of attenuation correction processing and scatter correction processing.

(Item 5)

The attenuation coefficient image generation method as recited in the above-described Item 1, wherein the step of generating the input image includes a step of performing processing including back projection processing on the measurement data.

(Item 6)

The attenuation coefficient image generation method as recited in the above-described Item 1, wherein the input image includes at least one of an image in which image quality conversion processing is not applied to the measurement data subjected to imaging processing, an image in which image quality conversion processing is applied to the measurement data subjected to imaging processing, and an image in which area identification processing is applied to the measurement data subjected to imaging processing.

(Item 7)

The attenuation coefficient image generation method as recited in the above-described Item 1, wherein the input image includes images having two or more types of resolutions.

(Item 8)

The attenuation coefficient image generation method as recited in the above-described Item 1, wherein the step of generating the intermediate image includes a step of applying a machine learning model trained in advance to the input image.

(Item 9)

The attenuation coefficient image generation method as recited in the above-described Item 8, wherein the input image as training data of the machine learning model includes at least one of a normalized image in which a pixel value range is normalized, an image in which the normalized image is multiplied by a coefficient greater than 0 and smaller than 1, and an image in which a specific area of the normalized image or an image before normalization is multiplied by a positive coefficient.

(Item 10)

The attenuation coefficient image generation method as recited in the above-described Item 8, wherein the machine learning model simultaneously outputs, in addition to the intermediate image, a reconstructed image to which at least one of attenuation correction processing and scatter correction processing is applied.

(Item 11)

The attenuation coefficient image generation method as recited in the above-described Item 8, wherein the machine learning model includes at least one of a machine learning model in which a three-dimensional image is input, a machine learning model in which an axial cross-sectional image is input, a machine learning model in which a coronal cross-sectional image is input, a machine learning model in which a sagittal cross-sectional image is input, a machine learning model in which a patch image extracted from a three-dimensional image is input, a machine learning model in which a patch image extracted from an axial cross-sectional image is input;

a machine learning model in which a patch image extracted from a coronal cross-sectional image is input, and a machine learning model in which a patch image extracted from a sagittal cross-sectional image is input.

(Item 12)

The attenuation coefficient image generation method as recited in the above-described Item 8, wherein the machine learning model is configured such that information relating to a spatial position of the input image is input in addition to the input image.

(Item 13)

The attenuation coefficient image generation method as recited in the above-described Item 8, wherein the machine learning model includes a deep neural network.

Item 14

The attenuation coefficient image generation method as recited in the above-described Item 13, wherein the deep neural network includes convolution processing.

Item 15

The attenuation coefficient image generation method as recited in the above-described Item 8, wherein the machine learning model is trained using a pseudo image generated based on at least one of a Monte Carlo simulation calculation and an analytical simulation calculation.

Item 16

The attenuation coefficient image generation method as recited in the above-described Item 15, wherein the machine learning model is trained using both the pseudo images and actual images of the subjects.

Item 17

The attenuation coefficient image generation method as recited in the above-described Item 16, wherein the machine learning model is additionally trained using the actual images of the subjects with a machine learning model trained by the pseudo images as a base model.

Item 18

The attenuation coefficient image generation method as recited in the above-described Item 3, wherein the step of generating the attenuation coefficient image includes the steps of:

performing linear combination processing of the tissue composition ratio images of tissues in which known attenuation coefficients are set to weight coefficients, in a case where the intermediate image includes the tissue composition ratio image; and performing assignment processing of a known attenuation coefficient corresponding to a label value of the tissue label image, in a case where the intermediate image includes the tissue label image.

Item 19

The attenuation coefficient image generation method as recited in the above-described Item 3, wherein the step of generating the attenuation coefficient image includes a step of performing linear combination processing of certainty degree images that are intermediate output of the tissue label image in which known attenuation coefficients are set to weight coefficients, in a case where the intermediate image includes the tissue label image.

Item 20

The attenuation coefficient image generation method as recited in the above-described Item 1, wherein the measurement data is measurement data of a human head, and wherein the element constituting the image relating to the tissue area includes at least one of background, cavity, soft tissue, and bone.

Item 21

The attenuation coefficient image generation method as recited in the above-described Item 1, wherein the measurement data is measurement data of a human breast, and wherein an element constituting the image relating to the tissue area includes at least one of background and soft tissue.

Item 22

A nuclear medicine diagnostic apparatus comprising:

a detector configured to detect radiation generated from a radiopharmaceutical agent in a subject; and a processor configured to generate a radioactivity distribution image of the subject based on detection of the radiation by the detector, wherein the processor is configured to generate an input image by performing imaging processing on measurement data acquired based on detection of the radiation emitted from the subject, generate an intermediate image including an image relating to tissue areas based on the input image, and generate an attenuation coefficient image for generating the radioactivity distribution image, based on the intermediate image and known attenuation coefficients of the tissue areas.

Item 23

The nuclear medicine diagnostic apparatus as recited in the above-described Item 22, wherein the processor is configured to perform at least one of attenuation correction processing and scatter correction processing, based on the attenuation coefficient image.

Item 24

A trained model generation method for a nuclear medicine diagnostic apparatus, the method comprising the steps of:

preparing tissue label images indicating a tissue to which each pixel belongs;

generating pseudo-radioactivity distribution images and pseudo-attenuation coefficient images, based on the tissue label images;

generating pseudo-measurement data by performing simulation calculations, based on the pseudo-radioactivity distribution images and the pseudo-attenuation coefficient images;

generating pseudo images by performing imaging processing on the pseudo-measurement data; and generating a trained model using the pseudo images as training data.

DESCRIPTION OF SYMBOLS

1: PET device (nuclear medicine diagnostic apparatus)
2: Detector ring (detector)
5: Measurement data
6, **6*a***: Input image
7, **7*a***: Intermediate image
8: Machine learning model
9: Attenuation coefficient image
10: Radioactivity distribution image
11: Tissue label image
12: Pseudo-radioactivity distribution image
13: Pseudo-attenuation coefficient image
15: Pseudo-measurement data
16: Pseudo-reconstructed image (pseudo image)
20: Information for spatial location
21: Reconstructed image
41: Processing circuit (processor)
71: Tissue composition ratio image
72: Tissue label image
100: T: subject

The invention claimed is:

1. An attenuation coefficient image generation method for a nuclear medicine diagnostic apparatus for generating the attenuation coefficient image of a subject, the method comprising the steps of:

generating an input image by performing imaging processing on measurement data acquired based on detection of radiation emitted from the subject;

generating a plurality of tissue composition ratio images indicating ratios of a plurality of tissues included in each pixel or a plurality of certainty degree images indicating probability of whether each pixel belongs to one of a plurality of tissues, based on the input image; and generating an attenuation coefficient image based on weighting addition by multiplying each of the plurality of tissue composition ratio images or the plurality of certainty degree images by known attenuation coefficients of the plurality of tissues and then adding up each of the images multiplied by the known attenuation coefficients.

2. The attenuation coefficient image generation method as recited in claim 1, wherein the step of generating the attenuation coefficient image includes a step of assigning attenuation coefficients to tissues in the tissue composition ratio image or tissues in the certainty degree image, based on known attenuation coefficients.

3. The attenuation coefficient image generation method as recited in claim 1, wherein the step of generating the input image includes a step of generating the input image without performing at least one of attenuation correction processing or scatter correction processing.

4. The attenuation coefficient image generation method as recited in claim 1, wherein the step of generating the input image includes a step of performing processing including back projection processing on the measurement data.

5. The attenuation coefficient image generation method as recited in claim 1, wherein the input image includes at least one of an image in which image quality conversion processing is not applied to the measurement data subjected to imaging processing, an image in which image quality conversion processing is applied to the measurement data subjected to imaging processing, or an image in which area identification processing is applied to the measurement data subjected to imaging processing.

6. The attenuation coefficient image generation method as recited in claim 1, wherein the input image includes images having two or more types of resolutions.

7. The attenuation coefficient image generation method as recited in claim 1, wherein the step of generating the tissue composition ratio image or the certainty degree image includes a step of applying a machine learning model trained in advance to the input image.

8. The attenuation coefficient image generation method as recited in claim 7, wherein the input image as training data of the machine learning model includes at least one of a normalized image in which a pixel value range is normalized, an image in which the normalized image is multiplied by a coefficient greater than 0 and smaller than 1, or an image in which a specific area of the normalized image or an image before normalization is multiplied by a positive coefficient.

9. The attenuation coefficient image generation method as recited in claim 7, wherein the machine learning model simultaneously outputs, in addition to the tissue composition ratio image or the certainty degree image, a reconstructed image to which at least one of attenuation correction processing or scatter correction processing is applied.

10. The attenuation coefficient image generation method as recited in claim 7, wherein the machine learning model includes at least one of a machine learning model in which a three-dimensional image is input, a machine learning model in which an axial cross-sectional image is input, a machine learning model in which a coronal cross-sectional image is input, a machine learning model in which a sagittal cross-sectional image is input, a machine learning model in which a patch image extracted from a three-dimensional image is input, a machine learning model in which a patch image extracted from an axial cross-sectional image is input;

a machine learning model in which a patch image extracted from a coronal cross-sectional image is input, or a machine learning model in which a patch image extracted from a sagittal cross-sectional image is input.

11. The attenuation coefficient image generation method as recited in claim 7, wherein the machine learning model is configured such that information relating to a spatial position of the input image is input in addition to the input image.

12. The attenuation coefficient image generation method as recited in claim 7, wherein the machine learning model includes a deep neural network.

13. The attenuation coefficient image generation method as recited in claim 12, wherein the deep neural network includes convolution processing.

14. The attenuation coefficient image generation method as recited in claim 7, wherein the machine learning model is trained using pseudo images generated based on at least one of a Monte Carlo simulation calculation or an analytical simulation calculation.

15. The attenuation coefficient image generation method as recited in claim 14, wherein the machine learning model is trained using both the pseudo images and actual images of subjects.

16. The attenuation coefficient image generation method as recited in claim 15, wherein the machine learning model is additionally trained using the actual images of the subjects with a machine learning model trained by the pseudo images as a base model.

17. The attenuation coefficient image generation method as recited in claim 2, wherein the step of generating the attenuation coefficient image includes the steps of:

performing linear combination processing of the tissue composition ratio images of tissues in which known attenuation coefficients are set to coefficients, in a case where the tissue composition ratio image is generated.

18. The attenuation coefficient image generation method as recited in claim 2, wherein the step of generating the attenuation coefficient image includes a step of performing linear combination processing of the certainty degree images that are intermediate output of the certainty degree image in which known attenuation coefficients are set to weight coefficients, in a case where the certainty degree image is generated.

19. The attenuation coefficient image generation method as recited in claim 1, wherein the measurement data is measurement data of a human head, and wherein an element configuring the tissue composition ratio image or the certainty degree image includes at least one of background, cavity, soft tissue, or bone.

20. The attenuation coefficient image generation method as recited in claim 1, wherein the measurement data is measurement data of a human breast, and wherein an element configuring the tissue composition ratio image or the certainty degree image includes at least one of background or soft tissue.

21. A nuclear medicine diagnostic apparatus comprising:

a detector configured to detect radiation generated from a radiopharmaceutical agent in a subject; and a processor configured to generate a radioactivity distribution image of the subject based on detection of the radiation by the detector, wherein the processor is configured to generate an input image by performing imaging processing on measurement data acquired based on detection of the radiation emitted from the subject, generate a plurality of tissue composition ratio images indicating ratios of a plurality of tissues included in each pixel or a plurality of certainty degree images indicating probability of whether each pixel belongs to one of a plurality of tissues, based on the input image, and generate an attenuation coefficient image for generating the radioactivity distribution image, based on weighting addition by multiplying each of the plurality of tissue composition ratio images or the certainty degree images by known attenuation coefficients of the plurality of tissues and then adding up each of the images multiplied by the known attenuation coefficients.

22. The nuclear medicine diagnostic apparatus as recited in claim 21, wherein the processor is configured to perform at least one of attenuation correction processing or scatter correction processing, based on the attenuation coefficient image.

23. A trained model generation method for a nuclear medicine diagnostic apparatus, the method comprising the steps of:

preparing tissue label images indicating a tissue to which each pixel belongs;

generating pseudo-radioactivity distribution images generated by assigning radioactive concentration to each tissue of the tissue label images, corresponding to a radioactivity distribution image generated by the nuclear medicine diagnostic apparatus and pseudo-attenuation coefficient images generated by assigning an attenuation coefficient to each integrated tissue of the tissue label images, based on the tissue label images;

generating pseudo-measurement data corresponding to measurement data generated by the nuclear medicine diagnostic apparatus by performing simulation calculations, based on the pseudo-radioactivity distribution images and the pseudo-attenuation coefficient images;

generating pseudo images by performing imaging processing on the pseudo-measurement data, the pseudo images corresponding to an input image generated by the nuclear medicine diagnostic apparatus by performing imaging processing on the measurement data; and generating a trained model using the pseudo images based on the tissue label images as training input images and a plurality of tissue composition ratio images indicating ratios of a plurality of tissues included in each pixel based on the tissue label image as training output images.

* * * * *